US012631612B2

(12) United States Patent
Wang

(10) Patent No.: US 12,631,612 B2
(45) Date of Patent: May 19, 2026

(54) FLUORESCENT DYE MOLECULES FOR TRACER APPLICATIONS IN SUBTERRANEAN FORMATIONS

(71) Applicant: Saudi Arabian Oil Company, Dhahran (SA)

(72) Inventor: Wei Wang, Quincy, MA (US)

(73) Assignee: Saudi Arabian Oil Company, Dhahran (SA)

(*) Notice: Subject to any disclaimer, the term of this patent is extended or adjusted under 35 U.S.C. 154(b) by 1149 days.

(21) Appl. No.: 17/643,931

(22) Filed: Dec. 13, 2021

(65) Prior Publication Data

US 2023/0183565 A1 Jun. 15, 2023

(51) Int. Cl.

| | |
|---|---|
| ***G01N 33/24*** | (2006.01) |
| ***C09B 11/08*** | (2006.01) |
| ***C09B 11/24*** | (2006.01) |
| ***E21B 47/11*** | (2012.01) |
| ***G01N 21/64*** | (2006.01) |

(52) U.S. Cl.

CPC .............. *G01N 33/24* (2013.01); *C09B 11/08* (2013.01); *C09B 11/24* (2013.01); *E21B 47/11* (2020.05); *G01N 21/64* (2013.01); *G01N 2021/6497* (2013.01); *Y10T 436/13* (2015.01)

(58) Field of Classification Search

CPC .... G01N 33/24; G01N 33/2823; E21B 47/11; Y10T 436/13; C09B 11/08; C09B 11/24

See application file for complete search history.

(56) References Cited

U.S. PATENT DOCUMENTS

| | | | |
|---|---|---|---|
| 1,910,489 | A | 5/1933 | Lubs et al. |
| 2,033,949 | A | 3/1936 | Lubs et al. |
| 2,051,218 | A | 8/1936 | Magoun et al. |
| 2,061,243 | A | 11/1936 | Lubs et al. |
| 2,086,822 | A | 7/1937 | Schubert et al. |
| 2,339,621 | A | 1/1944 | D'Alelio et al. |
| 2,390,848 | A | 12/1945 | Richter |
| 2,455,894 | A | 12/1948 | Lecher et al. |
| 2,479,498 | A | 8/1949 | Lecher et al. |
| 2,885,421 | A | 5/1959 | Spiegler |
| 3,086,962 | A | 4/1963 | Mottus |

(Continued)

FOREIGN PATENT DOCUMENTS

| | | |
|---|---|---|
| EP | 0171978 | 11/1990 |
| EP | 1721603 | 11/2006 |

(Continued)

OTHER PUBLICATIONS

Cho, S. et al. "Lysosome-specific one-photon fluorescence staining and two-photon singlet oxygen generation by molecular dyad," RSC Adv., 2014, 4, 16913 (4 pages) (Year: 2014).*

(Continued)

*Primary Examiner* — Jennifer Wecker
*Assistant Examiner* — Michelle Adams
(74) *Attorney, Agent, or Firm* — Fish & Richardson P.C.

(57) ABSTRACT

A composition includes a functionalized fluorescent dye. The functionalized fluorescent dye includes an isothiocyanate-containing dye functionalized with a functional group. The functional group includes an aromatic compound with a primary amine. The functionalized fluorescent dye can be mixed with a fluid to form a tracer fluid for tracing fluid flow in a subterranean formation.

18 Claims, 6 Drawing Sheets

(56) References Cited

U.S. PATENT DOCUMENTS

| | | | |
|---|---|---|---|
| 3,103,467 | A | 9/1963 | Beaver |
| 3,238,176 | A | 3/1966 | Brooks et al. |
| 3,241,971 | A | 3/1966 | Kitze |
| 3,281,446 | A | 10/1966 | Manning |
| 3,287,136 | A | 11/1966 | McBride |
| 3,301,895 | A | 1/1967 | Sayigh et al. |
| 3,637,785 | A | 1/1972 | Smith et al. |
| 3,637,787 | A | 1/1972 | Rasschaert |
| 3,654,214 | A | 4/1972 | Beckman |
| 3,655,533 | A | 4/1972 | Page |
| 3,953,506 | A | 4/1976 | Spicer et al. |
| 3,953,606 | A | 4/1976 | Spicer et al. |
| 4,148,799 | A | 4/1979 | Enders |
| 4,461,821 | A | 7/1984 | Sano et al. |
| 4,772,563 | A | 9/1988 | Evangelista et al. |
| 4,921,939 | A | 5/1990 | Nofre et al. |
| 5,124,268 | A | 6/1992 | Dakubu |
| 5,168,927 | A | 12/1992 | Stegenneier |
| 5,498,502 | A | 3/1996 | Muramoto et al. |
| 5,677,120 | A | 10/1997 | Lushington et al. |
| 6,250,848 | B1 | 6/2001 | Moridis et al. |
| 6,331,436 | B1 | 12/2001 | Richardson et al. |
| 6,590,647 | B2 | 7/2003 | Stephenson |
| 6,691,780 | B2 | 2/2004 | Nguyen et al. |
| 7,032,662 | B2 | 4/2006 | Malone |
| 7,281,435 | B2 | 10/2007 | Sale et al. |
| 7,485,471 | B1 | 2/2009 | Sun et al. |
| 7,588,827 | B2 | 9/2009 | Nie et al. |
| 7,861,601 | B2 | 1/2011 | Sale et al. |
| 7,879,625 | B1 | 2/2011 | Boss |
| 8,269,501 | B2 | 9/2012 | Schmidt et al. |
| 8,337,783 | B2 | 12/2012 | Locascio et al. |
| 8,627,902 | B2 | 1/2014 | Hammer |
| 8,638,104 | B2 | 1/2014 | Barber et al. |
| 8,877,954 | B2 | 11/2014 | Giesenberg et al. |
| 9,034,920 | B2 | 5/2015 | Lam et al. |
| 9,080,097 | B2 | 7/2015 | Gupta et al. |
| 9,133,709 | B2 | 9/2015 | Huh et al. |
| 9,322,056 | B2 | 4/2016 | McCann et al. |
| 9,366,099 | B2 | 6/2016 | Ly |
| 9,594,070 | B2 | 3/2017 | Rule et al. |
| 10,273,399 | B2 | 4/2019 | Cox |
| 10,308,865 | B2 | 6/2019 | Cox |
| 10,308,895 | B2 | 6/2019 | Vidal et al. |
| 10,400,159 | B2 | 9/2019 | Gupta |
| 10,487,259 | B2 | 11/2019 | Cox |
| 10,927,292 | B2 | 2/2021 | Borrell et al. |
| 10,961,443 | B2 | 3/2021 | Zhao |
| 10,961,445 | B2 | 3/2021 | Ogle et al. |
| 2002/0161051 | A1 | 10/2002 | Chow et al. |
| 2003/0220204 | A1 | 11/2003 | Baran et al. |
| 2004/0108110 | A1 | 6/2004 | Zupanick et al. |
| 2005/0252286 | A1 | 11/2005 | Ibrahim et al. |
| 2006/0052374 | A1 | 3/2006 | Carroll et al. |
| 2006/0105052 | A1 | 5/2006 | Acar et al. |
| 2007/0114030 | A1 | 5/2007 | Todd et al. |
| 2008/0110253 | A1 | 5/2008 | Stephenson et al. |
| 2008/0111064 | A1 | 5/2008 | Andrews et al. |
| 2009/0087911 | A1 | 4/2009 | Rogerio |
| 2009/0087912 | A1 | 4/2009 | Ramos et al. |
| 2009/0248309 | A1 | 10/2009 | Nelville et al. |
| 2009/0277625 | A1 | 11/2009 | Bai et al. |
| 2010/0049625 | A1 | 2/2010 | Biebesheimer et al. |
| 2010/0092865 | A1 | 4/2010 | Kanno et al. |
| 2010/0224823 | A1 | 9/2010 | Yin et al. |
| 2010/0307745 | A1 | 12/2010 | Lafitte et al. |
| 2011/0012331 | A1 | 1/2011 | Kim |
| 2011/0030949 | A1 | 2/2011 | Weaver et al. |
| 2011/0207231 | A1 | 8/2011 | Natan et al. |
| 2011/0239754 | A1 | 10/2011 | Dyer et al. |
| 2011/0257887 | A1 | 10/2011 | Cooper et al. |
| 2011/0260051 | A1 | 10/2011 | Preudhomme et al. |
| 2011/0275061 | A1 | 11/2011 | Weidemaier et al. |
| 2012/0062886 | A1 | 3/2012 | Piotti et al. |
| 2012/0115128 | A1 | 5/2012 | Miller |
| 2012/0135080 | A1 | 5/2012 | Bromberg et al. |
| 2012/0193578 | A1 | 8/2012 | Pan et al. |
| 2012/0225274 | A1 | 9/2012 | Ishikawa et al. |
| 2012/0257199 | A1 | 10/2012 | Liu et al. |
| 2012/0261617 | A1 | 10/2012 | Pan et al. |
| 2012/0325465 | A1 | 12/2012 | Hammer et al. |
| 2013/0017610 | A1 | 1/2013 | Roberts et al. |
| 2013/0040292 | A1 | 2/2013 | Lopez et al. |
| 2013/0084643 | A1 | 4/2013 | Commarieu et al. |
| 2013/0087329 | A1 | 4/2013 | Hewitt et al. |
| 2013/0109261 | A1 | 5/2013 | Koene |
| 2013/0244914 | A1 | 9/2013 | Wu et al. |
| 2013/0259808 | A1 | 10/2013 | Chen et al. |
| 2013/0296453 | A1 | 11/2013 | Giesenberg et al. |
| 2013/0312970 | A1 | 11/2013 | Lafitte et al. |
| 2013/0341030 | A1 | 12/2013 | Brannon et al. |
| 2014/0060832 | A1 | 3/2014 | Mahoney et al. |
| 2014/0077121 | A1 | 3/2014 | Sun et al. |
| 2014/0120627 | A1 | 5/2014 | Rubino et al. |
| 2014/0124196 | A1 | 5/2014 | Sunde et al. |
| 2014/0186939 | A1 | 7/2014 | Peterman et al. |
| 2014/0190700 | A1 | 7/2014 | Tang et al. |
| 2014/0231077 | A1 | 8/2014 | Rivero et al. |
| 2014/0260694 | A1 | 9/2014 | Szlendak |
| 2014/0323363 | A1 | 10/2014 | Perriat |
| 2014/0360973 | A1 | 12/2014 | Yin et al. |
| 2015/0013983 | A1 | 1/2015 | Alwattari |
| 2015/0038347 | A1 | 2/2015 | Johnson et al. |
| 2015/0050741 | A1 | 2/2015 | Tour et al. |
| 2015/0079270 | A1 | 3/2015 | Wang et al. |
| 2015/0118501 | A1 | 4/2015 | Lu |
| 2015/0132543 | A1 | 5/2015 | Nouzille et al. |
| 2015/0159079 | A1 | 6/2015 | Huh et al. |
| 2015/0218379 | A1 | 8/2015 | Gee et al. |
| 2015/0232747 | A1 | 8/2015 | Kanj et al. |
| 2015/0268370 | A1 | 9/2015 | Johnston et al. |
| 2015/0368547 | A1 | 12/2015 | Lesko et al. |
| 2015/0376493 | A1 | 12/2015 | Huh et al. |
| 2016/0003040 | A1 | 1/2016 | Jessheim et al. |
| 2016/0040514 | A1 | 2/2016 | Rahmani et al. |
| 2016/0083641 | A1 | 3/2016 | Gamage |
| 2016/0097750 | A1 | 4/2016 | Van Herzen et al. |
| 2016/0215030 | A1 | 7/2016 | Bressner |
| 2016/0264846 | A1 | 9/2016 | Bennetzen et al. |
| 2016/0304934 | A1 | 10/2016 | Matsuno |
| 2017/0022804 | A1 | 1/2017 | Gupta et al. |
| 2017/0059668 | A1 | 3/2017 | Chang et al. |
| 2017/0199124 | A1 | 7/2017 | Bolduc et al. |
| 2017/0350236 | A1 | 12/2017 | Shen et al. |
| 2017/0361376 | A1 | 12/2017 | Murugesan et al. |
| 2018/0171782 | A1 | 6/2018 | Cox et al. |
| 2018/0275114 | A1 | 9/2018 | Kosynkin et al. |
| 2019/0118265 | A1 | 4/2019 | Nie et al. |
| 2019/0218907 | A1 | 7/2019 | Ow et al. |
| 2019/0226326 | A1 | 7/2019 | Ow et al. |
| 2019/0368336 | A1 | 12/2019 | Hammond et al. |
| 2019/0382648 | A1 | 12/2019 | Murugesan et al. |
| 2021/0025858 | A1 | 1/2021 | Ow et al. |
| 2023/0141596 | A1 | 5/2023 | Wang et al. |
| 2023/0141819 | A1 | 5/2023 | Wang et al. |
| 2023/0144199 | A1 | 5/2023 | Wang et al. |
| 2023/0182110 | A1 | 6/2023 | Wang et al. |
| 2023/0235218 | A1 | 7/2023 | Wang |

FOREIGN PATENT DOCUMENTS

| | | | | |
|---|---|---|---|---|
| EP | 2040075 | | | 3/2009 |
| EP | 2480625 | | | 4/2013 |
| EP | 2480626 | | | 4/2013 |
| GB | 2489714 | | | 10/2012 |
| JP | H08271430 | A | * | 10/1996 |
| JP | 2005524849 | | | 8/2005 |
| JP | 2007514169 | | | 5/2007 |
| JP | 2008505259 | | | 2/2008 |
| JP | 2008524602 | | | 7/2008 |
| JP | 2009535060 | | | 10/2009 |
| JP | 2009540326 | | | 11/2009 |
| JP | 2015523073 | | | 8/2015 |
| WO | WO 2010138914 | | | 12/2010 |

(56) References Cited

FOREIGN PATENT DOCUMENTS

| | | |
|---|---|---|
| WO | WO 2011035292 | 3/2011 |
| WO | WO 2011035294 | 3/2011 |
| WO | WO 2011063023 | 5/2011 |
| WO | WO 2012154332 | 11/2012 |
| WO | WO 2012158478 | 11/2012 |
| WO | WO 2013142869 | 9/2013 |
| WO | WO 2014014919 | 1/2014 |
| WO | WO 2014066793 | 5/2014 |
| WO | WO 2014096495 | 6/2014 |
| WO | WO 2014207075 | 12/2014 |
| WO | WO 2015044446 | 4/2015 |
| WO | WO 2015058206 | 4/2015 |
| WO | WO 2015097116 | 7/2015 |
| WO | WO 2015200060 | 12/2015 |
| WO | WO 2016087397 | 6/2016 |
| WO | WO 2017011328 | 1/2017 |
| WO | WO 2017136641 | 8/2017 |
| WO | WO 2017164822 | 9/2017 |
| WO | WO 2018085504 | 5/2018 |
| WO | WO 2018175763 | 9/2018 |
| WO | WO 2021092328 | 5/2021 |

OTHER PUBLICATIONS

Liu, J.-M. et al. "Determination of Trace Deoxyribonucleic Acid by Using Fluorescein Isothiocyanate-Phenosafranine as a Double-Luminescent Phosphorescence Probe," J Fluoresc (2011) 21:195-202 (Year: 2011).*

U.S. Appl. No. 17/454,176, filed Apr. 9, 2021, Wang et al.

U.S. Appl. No. 17/454,181, filed Nov. 9, 2021, Wang et al.

U.S. Appl. No. 17/522,437, filed Nov. 9, 2021, Wang et al.

U.S. Appl. No. 17/522,445, filed Nov. 9, 2021, Wang et al.

U.S. Appl. No. 17/548,837, filed Dec. 13, 2021, Wang.

U.S. Appl. No. 17/548,858, filed Dec. 13, 2021, Wang.

U.S. Appl. No. 17/549,062, filed Dec. 13, 2021, Wang.

Agenet et al., "SPE 157019: Fluorescent Nanobeads: a First Step Toward Intelligent Water Tracers" Society of Petroleum Engineers, SPE International Oilfield Nanotechnology conference, Jun. 12-14, 2012, 13 pages.

Alley et al., "Analysis of Polychlonnated Biphenyls in Fatty Biological Matrixes by On-Line Supercritical Fluid Extraction and Supercritical Fluid Cleanup." Journal of AOAC International 78.4, Jul. 1995, 1051-1054, 4 pages.

Anisimov, "SPE 118862: The Use of Tracers for Reservoir Characterization" Society of petroleum Engineers (SPE), presented at SPE Middle East Oil and Gas Show and Conference, Mar. 15-18, 2009, 8 pages.

Armelao et al., "Design of luminescent lanthanide complexes: From molecules to highly efficient photo-emitting materials" Coordination Chemistry Reviews, vol. 254, 5-6, Mar. 2010, 19 pages.

Aslan et al., "Fluorescent Core—Shell AG@$SiO_2$ Nanocomposites for Metal-Enhanced Fluorescence and Single Nanoparticle Sensing Platforms" Jan. 19, 2007, 2 pages.

Badgett et al., "Totalsynthese eines Neobetanidin-Derivates und des Neobetenamins" Helvetica Chimica Acta, 1970, 53(2): 433-448, 16 pages (English Abstract).

Bagaria et al., "Iron Oxide Nanoparticles Grafted with Sulfonated Copolymers are Stable in Concentrated Brine at Elevated Temperatures and Weakly Adsorb on Silica" ACS Applied Materials & Interfaces, vol. 5, No. 8, Mar. 25, 2013, 3329-3339, 11 pages.

Bala et al., "Interaction of Different Metal Ions with Carboxylic Acid Group: A Quantitative Study" The Journal of Physical Chemistry A, vol. 111, No. 28, Jun. 2007, 6183-6190, 8 pages.

Bao et al., "Luminescence properties of the co-luminescence groups of Sm-La-pyridyl carboxylic acids" Journal of Rare Earths, 30(4), Apr. 2012, 320-324, 5 pages.

Blachier et al., "Adsorption of polyamine on clay minerals" Journal of Colloid and Interface Science, 336, Aug. 2009, 599-606, 8 pages.

Borrini et al., "Water Soluble PDCA Derivatives for Selective Ln(III)/An(III) and Am(III)/Cm(III) Separation" Solvent Extraction and Ion Exchange, 33(3), Oct. 2014, 224-235, 30 pages.

Brichart et al., "The Use of Fluorescent Tracers for Inhibitor Concentration Monitoring Useful for Scale Inhibitor" International Petroleum Technology Conference, IPTC-17933-MS, presented at the International Petroleum Technology Conference held in Kuala Lumpur, Malaysia, Dec. 10-12, 2014, 8 pages.

Bunzil et al., "Taking advantage of luminescent lanthanide ions" Chemical Society Reviews, Dec. 2005, 29 pages.

Cao et al., "Solute reactive tracers for hydrogeological applications: A short review and future prospects." Water 12.3, Mar. 2020, 21 pages.

Chang et al., "Magnetic SERS Composite Nanoparticles for Microfluidic Detection" 251st ACE National Meeting, Mar. 13-17, 2016, 1 page.

Chemspider.com [online], "Structure Search" Mar. 2008, [retrieved on Feb. 15, 2022], retrieved from : URL <http://www.chemspider.com/structuresearch.aspx>, 1 page.

Chen et al., "Aggregation Kinetics of Alginate-Coated Hematite Nanoparticles in Monovalent and Divalent Electrolytes" Environmental Science & Technology, vol. 40, No. 5, Mar. 2006, 1516-1523, 9 pages.

Chen et al., "Analysis of the solution conformations of T4 lysozyme by paramagnetic NMR spectroscopy" Physical Chemistry Chemical Physics, 2016, 18(8), 5850-5859, 10 pages.

Chen et al., "Impact of Irreversible Retention on Tracer Deployments; Constraining Novel Material Deployments" SPE 188890-MS, in SPE Abu Dhabi International Petroleum Exhibition and Conference, Society of Petroleum Engineers, Nov. 2017, 8 pages.

Chen et al., "Improved Reservoir History Matching and Prudction Optimization with Tracer Data" SPE 191523-MS, in SPE Annual Technical Conference and Exhibition, Society of Petroleum Engineers, Sep. 2018, 15 pages.

Chen et al., "Upconversion Nanoparticles: Design, Nanochemistry, and Applications in Theranostics" Chem. Rev, 114(10), Mar. 2014, 5161-5214, 54 pages.

Chen et al., "FITC functionalized magnetic core-shell $Fe_3O_4$/Ag hybrid nanoparticle for selective determination of molecular biothiols" Elsevier Ltd., Dec. 2013, 7 pages.

Chen et al.; "Hydration Repulsion between Carbohydrate Surfaces Mediated by Temperature and Specific Ions" Scientific Reports, vol. 6, Jun. 23, 2016, 10 pages.

Cheraghian, "Application of nano-particles of clay to improve drilling fluid" Int. J. Nanosci. Nanotechnol., 13, Jun. 2017, 177-186, 10 pages.

Chuang et al., "Ultra-sensitive in-situ detection of novel near-infrared persistent luminescent tracer nanoagents in crude oil-water mixtures" a natureresearch journal, Scientific Reports, Jun. 15, 2016, 5 pages.

Coates et al., "Enhancement of luminescence of europium(m) ions in water by use of synergistic chelation. Part 1.1 : 1 and 2 : 1 complexes" J. Chem. Soc, Perkin Trans., Jan. 1996, 1275-1282, 8 pages.

Cole et al.; "Polyethylene Glycol Modified, Cross-Linked Starch-Coated Iron Oxide Nanoparticles for Enhanced Magnetic tumor Targeting" Biomaterials, vol. 32, No. 8, Mar. 1, 2011, 2183-2193, 11 pages.

Cox et al., "Pyrolyzable Nanoparticle Tracers for Environmental Interrogation and Monitoring" ACS Appl. Mater. Interfaces, 2017, 9(15), 13111-13120, 10 pages.

Cubillos et al., "SPE 174394-MS: The Value of Inter-well and Single Well Tracer Technology for De-Risking and Optimizing a CEOR Process—Caracara Field Case" Society of Petroleum Engineers (SPE), presented at EUROPEC 2015, Jun. 1-4, 2015, 19 pages.

Das et al., "Molecular Fluorescence, Phosphorescence, and Chemiluminescence Spectrometry" Analytical Chemistry, Nov. 3, 2011, 29 pages.

Deans, "SPE 7076: Using Chemical Tracers To Measure Fractional Flow And Saturation In-Situ" Society of Petroleum Engineers (SPE), presented at SPE Symposium on improved Methods of Oil Recovery, Apr. 16-17, 1978, 10 pages.

(56) References Cited

OTHER PUBLICATIONS

Deschamps et al., "Drilling to the Extreme: the Micro-Coring Bit Concept" IADC/SPE 115187, presented at the IADC/SPE Asai Pacific Drilling Technology Conference and Exhibition, Aug. 25-27, 2008, 12 pages.
Desmette et al., "Drilling Hard and Abrasive Rock Efficiently, or Generating Quality Cuttings? You No Longer Have to Choose . . . " SPE 116554, Society of Petroleum Engineers, 2008 SPE Annual Technical Conference and Exhibition, Sep. 21-24, 2008, 19 pages.
Du et al., "SPE 93140: Interwell Tracer Tests: Lessons Learnted from past Field Studies" Society of Petroleum Engineers (SPE), presented at SPE Asia Pacific Oil and Gas Conference and Exhibition, Apr. 5-7, 2005, 9 pages.
Dugstad, "Chapter 6: Well-to-well tracer tests" in Petroleum Engineering Handbook, 2007, 651-683, 31 pages.
Dung et al., "Structural and magnetic properties of starch coated magnetite nanoparticles" Journal of Experimental Nanoscience, 4, Sep. 2009, 259-267, 9 pages.
Edwards et al., "Extending the distance range accessed with continuous wave EPR with Gd3+ spin probes at high magnetic fields" Physical Chemistry Chemical Physics, 15(27), 2013, 11313-11326, 14 pages.
El-Aneed et al., "Mass Spectrometry, Review of the Basics: Electrospray, MALDI, and Commonly Used Mass Analyzers" Applied Spectroscopy Reviews, Mar. 16, 2009, 22 pages.
Fichtel et al., "A highly sensitive HPLC method for determination of nanomolar concentrations of dipicolinic acid, a characteristic constituent of bacterial endospores" Journal of Microbiological Methods, 2007, 70, 319-327, 9 pages.
Flury et al., "Dyes as tracers for vadose zone hydrology." Reviews of Geophysics 41.1, Mar. 2003, 37 pages.
Freeze and Cherry, "Chapter 9: Groundwater Contamination" in Groundwater, Englewood Cliffs, NJ: Prentice-Hall, Inc., 1979, 80 pages.
Galdiga and Greibrokk, "Ultra-trace determination of flurinated aromatic carboxylic acids in aqueous reservoir fluids using solid-phase extraction in combination with gas chromatography-mass spectrometry" Journal of Chromatography, vol. 793, Issue 2, Apr. 1997, 297-306, 10 pages.
Gao et al., "A Surface Functional Monomer-Directing Strategy for Highly Dense Imprinting of TNT at Surface of Silica Nanoparticles" Journal of American Chemical Society, vol. 129, No. 25, Jun. 2007, 7859-7866, 8 pages.
Gardiner et al., "Practical Raman Spectroscopy" Springer-Verlag, 1989, 9 pages.
Ge et al., "Fluorescence modified chitosan coated magnetic nanoparticles for high-efficienct cellular imaging" Nanoscale Res. Lett, 4, Jan. 2009, 287-295, 9 pages.
George et al., "Modified Dipicolinic Acid Ligands for Sensitation and Europium (III) Luminescence" Inorganic Chemistry, vol. 45, No. 4, Feb. 1, 2006, 6 pages.
Georgi, et al., "Advances in Cuttings Collection and Analysis" SPWLA 34th Annual Logging Symposium, Jun. 13-16, 1993, 20 pages.
Gordon-Grossman et al., "W-Band pulse EPR distance measurements in peptides using Gd3+-dipicolinic acid derivatives as spin labels" Physical Chemistry Chemical Physics, 13(22), 2011, 10771-10780, 10 pages.
Grutzke et al., "Heptacoordinate Heteroleptic Salan (ONNO) and Thiosalan (OSSO) Titanium(IV) Complexes: Investigation of Stability and Cytotoxicity" Inorganic Chemistry 54(14), Jul. 2015, 6697-6706, 10 pages.
Hagoot, "The response of interwell tracer tests in watered-out reservoirs" SPE 11131-MS, in SPE Annual Technical Conference and Exhibition, Society of Petroleum Engineers, Jan. 1982, 21 pages.
Han et al., "Application of Silver-Coated Magnetic Microspheres to a SERS-Based Optofluidic Sensor" The Journal of Physical Chemistry (JPCC), Mar. 7, 2011, 7 pages.
Hardy et al., "A novel fluorescent tracer for real-time tracing of clay transport over soil surfaces" Catena, 141, Jun. 2016, 39-45, 7 pages.
He et al., "Luminescent Europium Chelates Synthesis and Fluorescence Properties" Sensors and Materials (2007), 19(2), 123-132, 10 pages.
Hindle et al., "Dipicolinic acid (DPA) assay revisited and appraised for spore detection" Analyst, 1999, 124: 1599-1604, 6 pages.
Hu et al., "Smart Liquid SERS Substrates based on $Fe_3O_4$/Au Nanoparticles with Reversibility Tunable Enhancement Factor for Practical Quantitative Detection" a natureresearch journal, Scientific Reports, Nov. 27, 2014, 10 pages.
Huseby et al., "Assessing EOR potential from partitioning tracer data" Spe 172808-MS, in SPE Middle East Oil and Gas Show and Conference, Society of Petroleum Engineers, Mar. 2015, 15 pages.
Huseby et al., "SPE-169183-MS: High Quality Flow Information from Tracer Data" Society of Petroleum Engineers (SPE), presented at the SPE Bergen One Day Seminar, Apr. 2, 2014, 9 pages.
Hutchins et al., "SPE-21049: Aqueous Tracers for Oilfield Applications" Society of Petroleum Engineers (SPE), presented at SPE International Symposium on Oilfield Chemistry, Feb. 20-22, 1991, 9 pages.
Invitrogen, "Fluorophores and Their Amine-Reactive Derivatives" Molecular Probs Handbook, A Guide to Fluorescent Probes and Labeling Technologies, 11th Edition, 2010, 88 pages.
Jenkins et al., "Ultratrace Determination of Selected Lanthanides by Luminescence Enhancement" Analytical Chemistry, vol. 68, No. 17, Jan. 1, 1996, 7 pages.
Jun et al., "Multifunctional Silver-Embedded Magnetic Nanoparticles as SERS Nanoprobes and Their Applications" Wiley-VCH Verlag GmbH& Co. KGaA, Weinheim, Jan. 4, 2010, 7 pages.
Kaushik et al., "Gd(III) and Mn(II) complexes for dynamic nuclear polarization: small molecular chelate polarizing agents and applications with site-directed spin labeling of proteins" Physical Chemistry Chemical Physics, 18(39), 2016, 27205-27218, 36 pages.
Khalil et al., "Organic dye for subsea flowline assessment." SPE International Symposium on Oilfield Chemistry. OnePetro, Feb. 1999, 7 pages.
Khan et al., "Optimizing waterflood management in a giant UAE carbonate oil field using simulation-based streamlines" SPE 171777-MS, in Abu Dhabi International Petroleum Exhibition and Conference, Society of Petroleum Engineers, Nov. 10-13, 2014, 9 pages.
Kneipp et al., "Single Molecule Detection Using Surface-Enhanced Raman Scattering (SERS)" Physical Review Letters, American Physical Society vol. 78, No. 9, Mar. 3, 1997, 4 pages.
Kornberger and Thiele, "Experiences with an Efficient Rate-Management Approach for the 8th Tortonian Reservoir in the Vienna Basin" SPE 166393-PA, SPE Reservoir Evaluation and Engineering, vol. 17, No. 2, May 2014, 12 pages.
Kosynkin and Alaskar, "Oil Industry First Interwell Trial of Reservoir Nanoagent Tracers" SPE 181551-MS, in SPE Annual Technical Conference and Exhibition, Society of Petroleum Engineers, Sep. 2016, 15 pages.
Kramer, "Water-Soluble Dendritic Architectures with Carbohydrate Shells for the Templation and Stabilization of Catalytically Active Metal Nanoparticles" published by ACS, Macromolecules, vol. 38, No. 20, Aug. 27, 2005, 8308-8315, 8 pages.
Labbe et al., "Development of metal-chelating inhibitors for the Class II fructose 1,6-bisphosphate (FBP) aldolase" Journal of Inorganic Biochemistry, 112, Jul. 2012, 49-58, 10 pages.
Lachowicz et al., "Biocompatible and fluorescent superparamagnetic iron oxide nanoparticles with superior magnetic properties coates with charged polysaccharide derivatives" Colloids and Surfaces B: Biointerfaces, 2017, 150, 402-407, 18 pages.
Larsen et al., "Efficient Synthesis of 4,7-Diamino Substituted 1,10-Phenanthroline-2,9-dicarboxamides" Organic Letters, vol. 13, No. 13, Jul. 2011, 3546-3548, 3 pages.
Li et al., "An amino-endcapped octadecylsilane silica-based mixed-mode stationary phase for the simultaneous separation of neutral and ionizable components in fixed-dose combinations." Analytical Methods 11.30, 2019, 3898-3909, 12 pages.
Li et al., "Long persistent phosphors—from fundamentals to applications" Chem. Soc. Rev., 45(8), Apr. 2016, 2090-2136, 48 pages.

(56) References Cited

OTHER PUBLICATIONS

Li et al., "Magic Angle Spinning NMR Structure Determination of Proteins from Pseudocontact Shifts" Journal of the American Chemical Society, 135(22), May 2013, 8294-8303, 10 pages.
Li et al., "Superparamagnetic Iron Oxide Nanoparticles as MRI contrast agents for Non-invasive Stem Cell Labeling and Tracking" Theranostics, Jul. 2013, 3(8):595-615, 21 pages.
Li et al., "Thiol-ene reaction: a versatile tool in site-specific labelling of proteins with chemically inert tags for paramagnetic NMR" Chemical Communications, Cambridge, United Kingdom, 48(21), 2704-2706, 2012, 18 pages; Supporting Information only.
Liu et al., "Photostimulated near-infrared persistent luminescence as a new optical read-out from Cr3+- doped LiGa5O8" Scientific Reports 3, Article 1554, Mar. 2013, 9 pages.
Liu et al., "Separation of polyethylene glycols and their fluorescein-labeled compounds depending on the hydrophobic interaction by high-performance liquid chromatography." Journal of Chromatography A 1129.1, Sep. 2006, 61-66, 6 pages.
Lomstein and Jorgensen, "Pre-column liquid chromatographic determination of dipicolinic acid from bacterial endospores" Limnology and Oceanography: Methods, Apr. 2012, 10:4, 227-233, 14 pages.
Mahdavi et al., "Preparation, Characterization, and Application of Polyacrylamide-Polystyrene/Bentonite Nanocomposite as an Effective Immobilizing Adsorbent for Remediation of Soil" Chemistry Select, 5, Apr. 2020, 4538-4547, 12 pages.
Mahmoudi et al., "Superparamagnetic iron oxide nanoparticles development surface modification and applications in chemotherapy" Advanced Drug Delivery Reviews, Jan. 2011, 63, 24-46, 23 pages.
Manna et al., "Complexation behavior of trivalent actinides and lanthanides with 1,10-phenanthroline-2,9-dicarboxylic acid based ligands: insight from density functional theory" Physical Chemistry Chemical Physics, vol. 14, No. 31, Jan. 2012, 11060-11069, 10 pages.
Marais, A., et al. "Time-Resolved Fluorescence for Real-Time Monitoring of Both Scale and Corrosion Inhibitors: A Game-Changing Technique" SPE International Oilfield Scale Conference and Exhibition. OnePetro, May 2016, 11 pages.
Marchetti et al., "Fluorous affinity chromatography for enrichment and determination of perfluoroalkyl substances" Annual Review of Analytical Chemistry vol. 84, Jul. 19, 2012, 8 pages.
Martinez et al., "Polysaccharide-based Nanoparticles for Controlled Release Formulations" The Delivery of Nanoparticles, Published May 2012, 185-222, 40 pages.
Martini et al., "How to Monitor Scale Inhibitor Squeeze using Simple TRF Tracers" Society of Petroleum Engineers, presented at the SPE International Symposium on Oilfield Chemistry held in the Woodlands, Texas, Apr. 13-15, 2015, 8 pages.
McWilliams et al., "Fluorescent surfactants from common dyes-rhodamine B and eosin Y." Pure and Applied Chemistry 92.2, Feb. 2020, 265-274, 15 pages.
Melton et al., "Complexes of Greatly Enhanced Thermodynamic Stability and Metal Ion Size-Based Selectivity, Formed by the Highly Preorganized Non-Macrocyclic Ligand 1,10-Phenanthroline-2,9-dicarboxylic Acid: A Thermodynamic and Crystallographic Study" Inorganic Chemistry vol. 45 No. 23, Jun. 2006, 9 pages.
Moyner et al., "The Application of Flow Diagnostics for Reservoir Management" Society of Petroleum Engineers (SPE), Apr. 2015, 18 pages.
Muller and Seubert, "Ultra trace determination of fluorobenzoic acids in tap and reservoir water using solid-phase extraction and gas chromatography-mass spectrometry" Journal of Chromatography A, 1260, Oct. 2012, 7 pages.
Nie et al., "Probing Single Molecules and Single Nanoparticles by Surface-Enhanced Raman Scattering" Science, vol. 275, No. 5303, Feb. 1997, 1102-1106, 6 pages.
Ogden et al., "Complexation of Am(III) and Nd(in) by 1,10-Phenanthroli ne-2,9-Di carboxylic Acid" Journal of Solution Chemistry, vol. 42, No. 1, pp. 211-225, 2013, 15 pages.
Ouali et al., "Analysis of Paramagnetic NMR Spectra of Triple-Helical Lanthanide Complexes with 2,6-Dipicolinic Acid Revisited: A New Assignment of Structural Changes and Crystal-Field Effects 25 Years Later" Inorganic Chemistry, 41(6), Feb. 2002, 1436-1445, 10 pages.
Pallenberg et al. "Synthesis and Characterization of Some Copper(I) Phenanthroline Complexes" Inorg. Chem. 1995, 34, 2833-2840, 8 pages.
Park et al., "Application of montmorillonite in bentonite as a pharmaceutical excipient in drug delivery systems" Journal of Pharmaceutical Investigation, 46, May 2016, 363-375, 13 pages.
Parker and Williams, "Getting excited about lanthanide complexation chemistry" Journal of the Chemical Society, Dalton Transactions, vol. 18, 1996, 16 pages.
Parker et al., "Being excited by lanthanide coordination complexes: aqua species, chirality, excited-state chemistry, and exchange dynamics" Chemical Reviews, vol. 102, Issue 6, May 2002, 34 pages.
Petoud et al., "Brilliant SM, Eu, Tb, and Dy Chiral Lanthanide Complexes with Strong Circularly Polarized Luminescence" Journal fo the American Chemical Society (JACS), Dec. 15, 2006, 7 pages.
Potapov et al., "Nanometer-Scale Distance Measurements in Proteins Using Gd3+ Spin Labeling" Journal of the American Chemical Society, 132(26), Jun. 2010, 9040-9048, 9 pages.
Qianming et al., "Bspda Synthesis and its Europium (III) Complexes' Fluorescence" Chemical Industry Times, Jul. 2005, 19(7): 38-41, 4 pages (English Abstract).
Rashdan et al., "Effect of the preparation route, PEG and annealing on the phase stability of Fe3O4 nanoparticles and their magnetic properties" Journal of Experimental Nanoscience, vol. 8, No. 2, 2013, 210-222, 13 pages.
Rovani, "Enhanced Oil Recovery: Aqueous Flow Tracer Measurement" WRI-09-R002, OSTI.Gov, Technical Report, U.S. Department of Energy, Feb. 2009, 1-18, 25 pages.
Rowan et al., "Dynamic Covalent Chemistry" Angewante Chemie International Edition, Mar. 15, 2002, 55 pages.
Sabbatini et al., "Luminescent lanthanide complexes as photochemical supramolecular devices" Coordination Chemistry Reviews, vol. 123, issue 1-2, Feb. 1993, 28 pages.
Saeki et al., "Upper and lower critical solution temperatures in poly (ethylene glycol) solutions" Polymer, vol. 17, No. 8, Aug. 1976, 685-689, 5 pages.
Sammes and Yshioglu, "Modern bioassays using metal chelates as luminescent probes" Natural Product Reports, vol. 31, No. 1, 1996, 28 pages.
Sanni et al., "A field case study of inter-well chemical tracer test" in SPE International Symposium on Oilfield Chemistry, Society of Petroleum Engineers, Apr. 2015, 17 pages.
Sanni et al., "Pushing the envelope of residual oil measurement: A field case study of a new class of inter-well chemical tracers" Journal of Petroleum Science and Engineering, vol. 163, 2018, 19 pages.
Santarelli et al., "Formation Evaluation From Logging on Cuttings" SPE Reservoir Evaluation and Engineering, presented at the 1996 SPE Permian Basin Oil and Gas Recovery Conference, Mar. 27-29, 1996, published Jun. 1998, 7 pages.
Schmidt et al., "Copper dipicolinates as peptidomimetic ligands for the Src SH2 domain" Bioorganic & Medicinal Chemistry Letters, 14(16), 4203-4206, Aug. 2004, 4 pages.
Schmidt et al., "Synthesis of Mono- and Dinuclear Vanadium Complexes and Their Reactivity toward Dehydroperoxidation of Alkyl Hydroperoxides" Inorganic Chemistry 56(3), 2017, 1319-1332, 14 pages.
Selvin et al., "Principles and biophysical applications of lanthanide-based probes" Annual Review of Biophysics and Biomolecular Structure, Jun. 2002, 28 pages.
Serres-Piole et al., "Direct sensitive simultaneous determination of fluorinated benzoic acids in oil reservoir waters by ultra high-performance liquid chromatography-tandem mass spectrometry" Journal of Chromatography A, 1218, Aug. 2011, 6 pages.
Serres-Piole et al., "Water tracers in oilfield applications: Guidelines" Elsevier Ltd., Journal of Science and Engineering, Nov. 2012, 18 pages.

(56) References Cited

OTHER PUBLICATIONS

ShamsiJazeyi et al., "Polymer-Coated Nanoparticles for Enhance Oil Recovery" Journal of Applied Polymer Science, vol. 131, No. 15, Aug. 5, 2014, 13 pages.
Shook et al., "SPE 124614: Determining Reservoir Properties and Flood Performance from Tracer Test Analysis" Society of petroleum Engineers (SPE), presented at SPE Annual Technical Conference and Exhibition, Oct. 4-7, 2009, 19 pages.
Silva et al., "Studies on new chemical tracers for determination of residual oil saturation in the inter-well region. " SPE Oklahoma City Oil and Gas Symposium. OnePetro, Mar. 2017, 14 pages.
Solomon et al., "Synthesis and Study of Silver Nanoparticles" Journal of Chemical Education vol. 84, No. 2, 2007, 332-325, 4 pages.
Song et al., "SERS-Encoded Nanogapped Plasmonic Nanoparticles: Growth of Metallic Nanoshell by Templating Redox-Active Polymer Brushes" Journal of the American Chemical Society (JACS), Apr. 28, 2014, 4 pages.
Stiles et al., "Surface-Enhanced Raman Spectroscopy" Annual Review of Analytical Chemistry, vol. 1, No. 1, Jul. 2008, 601-626, 29 pages.
Stryer et al., "Diffusion-enhanced fluorescence energy transfer" Annual Review of Biophysics and bioengineering, vol. 11, Issue 1, 1982, 21 pages.
Su et al., "A Dipicolinic Acid Tag for Rigid Lanthanide Tagging of Proteins and Paramagnetic NMR Spectroscopy" Journal of the American Chemical Society, 130(32), Jul. 2008, 10486-10487, 2 pages.
Sýkora et al., "Recent advances in mixed-mode chromatographic stationary phases." Journal of separation science 42.1, Jan. 2019, 89-129, 75 pages.
Takenaka et al., "Effect of fatty acids on the membrane fluidity of cultured chick dorsal root ganglion measured by fluorescence photobleaching recovery." Journal of neurobiology 14.6, Nov. 1983, 457-461, 5 pages.
Tang et al., "Synthesis and fluorescence properties of Tb(III) complexes with pyridine-2,6-dicarboxylic acid derivatives" Journal of Central South University of Technology (English Edition), 15(5), Oct. 2008, 599-605, 7 pages.
Tang et al., "Synthesis of Novel Derivatives of Pyridine-2,6-dicarboxylic Acid" Synthetic Communications: An International Journal for Rapid Communication of Synthetic Organic Chemistry, 36(14), Jun. 2006, 2027-2034, 9 pages.
Tang et al., "Synthesis of Eu(III) and Tb(III) Complexes with Novel Pyridine-2,6-Dicarboxylic Acid Derivatives and Their Fluorescence Properties" Front. Chem. China, 2006, 4:, 408-413, 6 pages.
Thomas et al., "Deployment and Detection of a Novel Barcoded Advanced Tracers System for the Optimization of Improved Waterflood Recovery in Hydrocarbon Reservoirs" SPE-194872-MS, SPE Middle East Oil and Gas Show and Conference. Society of Petroleum Engineers, 2019, 10 pages.
Tian et al., "Off-Resonant Gold Superstructures as Ultrabright Minimally Invasive Surface-Enhanced Raman Scattering (SERS) Probes" American Chemical Society, Jul. 2015, 7 pages.
Toulhoat, "Experimentation and Modelling of U, Th and Lanthanides Transport in Fissured Rocks: Influence of Complexation" MRS Proceedings, vol. 50, Jan. 1, 1985, 8 pages.
Wahajuddin et al., "Superparamagnetic iron oxide nanoparticles: Magnetic nanoplatforms as drug carriers" International Journal of Nanomedicine, 7, Jul. 2012, 3445-3471, 27 pages.
Wang et al., "The Design and Implementation of a Full Field Inter-Well Tracer Program on a Giant UAE Carbonate Oil Field" in Abu Dhabi International Petroleum Exhibition and Conference, Society of Petroleum Engineers, SPE-177527-MS, Nov. 2015, 8 pages.
Wu et al., "A reusable biosensor chip for SERS-fluorescence dual mode immunoassay" Proc. SPIE 9543, Third International Symposium on Laser Interaction with Matter, 954317, May 4, 2015, 6 pages.
Wu et al., "A SERS-Assisted 3D Barcode Chip for High-Throughput Biosensing" Small Journal vol. 11, No. 23, Jun. 11, 2015, 9 pages.
Xu et al., "Superparamagnetic Photonic Crystals" Adv. Mater., Nov. 2001, 13, 1681-1683, 4 pages.
Xu et al., "Synthesis and Utilization of Monodisperse Superparamagnetic Colloidal Particles for Magnetically Controllable Photonic Crystals" Chem. Mater., 14(3), 2002, 1249-1256, 8 pages.
Xu et al.., "Measurement of two-photon excitation cross sections of molecular fluorophores with data from 690 to 1050 nm" Journal of the Optical Society of America B, Mar. 1996, 11 pages.
Yang et al., "The Co-Luminescence Groups of Sm-La-pyridyl Carboxylic Acids and the Binding Characteristics between the Selected Doped Complex and Bovine Serum Albumin" Bulletin of the Korean Chemical Society 33(4), Apr. 20, 2012, 1303-1309, 7 pages.
Yang et al., "Paramagnetic labeling of proteins and pseudocontact shift in structural biology" Chinese Journal of Magnetic Resonance, 2014, 31(2): 155-171, 12 pages (English Abstract).
Yu et al., "Adsorption of proteins and nucleic acids on clay minerals and their interactions: A review" Applied Clay Science, 80-81, Aug. 2013, 443-452, 10 pages.
Zamberi et al., "SPE 166005: Improved Reservoir Surveillance Through Injected Tracers In A Saudi Arabian Field: Case Study" Society of Petroleum Engineers (SPE), presented at SPE Reservoir Characterization and Simulation Conference and Exhibition, Sep. 2013, 15 pages.
Zemel, "Chapter 3: Interwell Water Tracers" Tracers in the Oil Field, vol. 43, 1st Edition, Elsevier Science, Jan. 13, 1995, 47 pages.
Zhang et al., "Water adsorption on kaolinite and illite after polyamine adsorption" Journal of Petroleum Science and Engineering, 142, Jun. 2016, 13-20, 8 pages.
Zhao et al., "Chromatographic Separation of Highly Soluble Diamond Nanoparticles Prepared by Polyglycerol Grafting" Angewandte Chemie International Edition, vol. 50, No. 6, Feb. 7, 2011, 1388-1392, 5 pages.
Zheng et al., "Immobilization of Candida rugosa lipase on hydrophobic/strong cation-exchange functional silica particles for biocatalytic synthesis of phytosterol esters." Bioresource technology 115, Jul. 2012, 141-146, 6 pages.
Zhou et al., "Upconversion luminescent materials: advances and applications" Chem Rev., Jan. 14, 2015, 71 pages.
Ghanem et al., "Investigation of Fluorescent Dyes as Partitioning Tracers for Subsurface Nonaqueous Phase Liquid (NAPL) Characterization," Journal of Enviornmental Engineering, Aug. 2003, 5 pages.
Feher et al., "Embedding resorcinarene cavitands in lipid vesicles," New Journal of Chemistry, Jan. 2012, 36(4):874-876, 3 pages.
Liu et al., "Self-Aggregating Deep Cavitand Acts as a Fluorescence Displacement Sensor for Lysine Methylation," J. Am. Chem. Soc., 2016, 138: 10746-10749, 4 pages.
Kim et al. "Molecular Tripods Showing Fluorescence Enhancement upon Binding to Streptavidin," Org. Lett., 2005, 7(1):111-114, 14 pages.
Lin et al. "Toward live-cell imaging of dopamine neurotransmission with fluorescent neurotransmitter analogues," Chem. Commun., 2015, 51, 14080-14083, 35 pages.
Okuno et al., "Thermoresponsive Carbohydrate-b-Polypeptoid Polymer Vesicles with Selective Solute Permeability and Permeable Factors for Solutes," Biomacromolecules, Jun. 24, 2021, 22, 3099-3106, 20 pages.
Seydack et al., "trans-Stilbene Photochemistry Beyond 500 nm," Journal of Fluorescence, 2000, 10(3), 291-294, 4 pages.
Amendola et al, "The interaction of fluoride with fluorogenic ureas: an ON/\1-OFF-ON/\2 response," Journal of the American Chemical Society, 2013, 135, 6345-6355, 11 pages.
Berry et al, "Fluorescent transmembrane anion transporters: shedding light on anionophoric activity in cells," Chemical Science, 2016, 7:5069-5077, 9 pages.
Byrne et al, "Urea and thiourea based anion receptors in solution and on polymer supports," Supramolecular Chemistry, 2018, 30:196-205, 10 pages.

(56) References Cited

OTHER PUBLICATIONS

Campbell et al, "p-Methoxyphenylisothiocyanate as a Reagent for the Identification of Amines," Proceedings of the Indiana Academy of Science, 1943, 53:119-121, 3 pages.
Cui et al, "Fluorescent investigation of the interactions between N-(p-chlorophenyl)-N'-(1-naphthyl) thiourea and serum albumin: Synchronous fluorescence determination of serum albumin," Analytica Chimica Acta, 2006, 571:175-183, 9 pages.
Dieke et al, "The acute toxicity of thioureas and related compounds to wild and domestic Norway rats," Journal of Pharmacology and Experimental Therapeutics, 1947, 90:260-270, 11 pages.
Dos Santos et al, "Selective fluorescent sensing of chloride," Supramolecular Chemistry, 2008, 20:407-418, 5 pages.
Dos Santos et al, "Synthesis, Structural and Photophysical Evaluations of Urea Based Fluorescent PET Sensors for Anions," Tetrahedron Letters, 2007, 48, 3135-3139, 13 pages.
Fesenko et al, "Different pathways in the reaction of N-(tosylmethyl)-substituted ureas, thioureas, and N'-cyanoguanidines with sodium cyanide. Synthesis of α-ureido nitriles, a-ureido amides, and hydantoin imino derivatives," Tetrahedron, 2020, 76(40), 18 pages.
French et al., "Alpha-naphthylisocyanate as a reagent for phenols for aliphatic amines/\1," Journal of the American Chemical Society, 1926, 48:1736-1739, 4 pages.
Gomez et al., "Urea vs. thiourea in anion recognition," Organic & Biomolecular Chemistry, 2005, 3:1495-1500, 7 pages.
Gunnlaugsson et al., "Design, synthesis and photophysical studies of simple fluorescent anion PET sensors using charge neutral thiourea receptors," Organic & Biomolecular Chemistry, 2004, 2:1856-1863, 8 pages.
Hacker et al, "Aromatic 2-(Thio)ureidocarboxylic Acids As a New Family of Modulators of Multidrug Resistance-Associated Protein 1: Synthesis, Biological Evaluation, and Structure-Activity Relationships," Journal of Medicinal Chemistry, 2009, 52:4586-45, 10 pages.
Ikedu et al, "Kinetics of Hydrogen Bonding between Anthracene Urea Derivatives and Anions in the Excited State," The Journal of Physical Chemistry A, 2011, 115:8227-8233, 7 pages.
Kim et al, "Novel Solid-Phase Parallel Synthesis of N-Substituted-2-aminobenzo [d]thiazole Derivatives via Cyclization Reactions of 2-Iodophenyl Thiourea Intermediate Resin," ACS Combinatorial Science, 2013, 15, 29-40, 12 pages.
Kinsella et al, "Synthesis and NMR Binding Studies towards Rational Design of a Series of Electron-Withdrawing Diamide Receptors/Organocatalysts," European Journal of Organic Chemistry, 2011, 1125-1132, 42 pages.
Kwon et al, "Unique hydrogen bonds between 9-anthracenyl hydrogen and anions," Journal of Organic Chemistry, 2004, 69:5155-5157, 3 pages.
Li et al, "A new and efficient solid state synthesis of diaryl thioureas," Synthetic Communications, 2001, 31:781-785, 5 pages.
Lin et al, "A new selective colorimetric and fluorescent sensor for Hg2+ and Cu2+ based on a thiourea featuring a pyrene unit, " Talanta, 2010, 81:1209-1215, 7 pages.
Muller et al, "N,N'-Disubstituted guanidine high potency sweeteners," Journal of Medicinal Chemistry, 1992, 35:740-743, 4 pages.
Nishizawa et al, "Anion recognition by a pyrene derivative with a thiourea function," Analytical Sciences, 1997, 13, supplement, 485-488, 4 pages.
Rahman et al, "Thiourea Derivatives, Simple in Structure but Efficient Enzyme Inhibitors and Mercury Sensors," Molecules, 2021, 26, 16 pages.
Ros-Lis et al, "Signaling Mechanisms in Anion-Responsive Push-Pull Chromophores: The Hydrogen-Bonding, Deprotonation and Anion-Exchange Chemistry of Functionalized Azo Dyes," European Journal of Organic Chemistry 2007, 2449-2458, 10 pages.
Sah, "p-bromo phenyl isothiocyanate as a reagent for the identification of aromatic amines," Journal of the Chinese Chemical Society, 1934, 2:225-228, 5 pages.
Suter et al, "Alpha-Naphthyl Isothiocyanate as a Reagent for Primary and Secondary Aliphatic Amines," Journal of the American Chemical Society, Jun. 1933, 55:2497-2499, 3 pages.
Wu et al, "Synthesis and biological evaluation of novel anti-hepatitis C virus (HCV) agents: 2-hydroxylphenethyl sulfanyl-oxopyrimidines," Medicinal Chemistry Research, 2017, 26:1388-1396, 9 pages.
Xie et al, "Study on host-guest complexation of anions based on a tripodal naphthylurea derivatives," Journal of the Chemical Society, Perkin Transactions 2, 1999, 2:2751-2754, 5 pages.
Ahn et al., "Privileged Structure-based Discovery of Novel 2-Iminothiazoles as Protein Tyrosine Phosphatase 1B Inhibitors," Bulletin of the Korean Chemical Society, Oct. 2013, 34(10):2861-2862, 2 pages.
Bock et al., "Sulfide Analogues of Flupirtine and Retigabine with Nanomolar KV7.2/KV7.3 Channel Opening Activity," ChemMedChem, Mar. 2019, 14(9):952-964, 104 pages.
Busschaert et al., "Towards Predictable Transmembrane Transport: QSAR Analysis of Anion Binding and Transport," Chemical Science, May 2013, 4:3036-3045, 11 pages.
Dud et al., "Synthesis of Monosubstituted Thioureas by Vapour Digestion and Mechanochemical Amination of Thiocarbamoyl Benzotriazoles," Green Chemistry, Mar. 2016, 18(9):2666-2674, 9 pages.
Dyson et al., "The Synthesis of Alkylthiocarbimides and their Thiocarbamide Derivatives by Means of Thiocarbonyl Chloride," Recueil des Travaux Chimiques des Pays-Bas, 1926, 45:421-423, 4 pages.
Janovec et al., "9-Isothiocyanatoanthracene as a Versatile Starting Compound in the Chemistry of Anthracen-9-yl Derivatives," Collect. Czech. Chem. Commun., Apr. 2002, 67(5):665-678, 14 pages.
Jun et al., "Anthracene derivatives bearing thiourea group as fluoride selective fluorescent and colorimetric chemosensors," Tetrahedron Letters, May 2006, 47(18):3103-3106, 4 pages.
Kumavat et al., "Green Synthesis of Symmetrical N, N'-disubstituted Thiourea Derivatives in Water Using Solar Energy," Environmental Chemistry Letters, Jan. 2013, 11:177-182, 6 pages.
Lindahl et al., "Determination of Volatile Amines in Air by Diffusive Sampling, Thiourea Formation and High-Performance Liquid Chromatography," Journal of Chromatography, Jul. 1993, 643(1-1):35-41, 7 pages.
Luo et al., "Synthesis and Biological Evaluation of Arylthiourea Derivatives with Antitubercular Activity," Letters in Drug Design & Discovery, Jul. 2013, 10(7):1-11, 11 pages.
Mayr et al., "A Chiral Thiourea as a Template for Enantioselective Intramolecular [2 + 2] Photocycloaddition Reactions," The Journal of Organic Chemistry, Jun. 2016, 81(16):6965-6971, 80 pages.
Mi et al., "Covalent Binding to Tubulin by Isothiocyanates—A Mechanism of Cell Growth Arrest and Apoptosis," The Journal of Biological Chemistry, Jun. 2008, 283(32):22136-22146, 11 pages.
Techapanalai, "Tetrabromomethane-mediated Desulfurization for Synthesis of Isothiocyanates from Amines," Thesis for the degree of Master of Science in Chemistry, Chulalongkorn University, 2020, 160 pages.
Webbook.nist.gov [online], "1-Aminofluorene," available on or before Jan. 30, 2024, via Internet Archive: Wayback Machine URL <https://webbook.nist.gov/cgi/cbook.cgi?ID=C6344634&Mask=2780#Refs>, retrieved on Jan. 30, 2024, 3 pages.
Webbook.nist.gov [online], "2-Fluorenamine," available on or before Jan. 30, 2024, via Internet Archive: Wayback Machine URL <https://webbook.nist.gov/cgi/cbook.cgi?ID=C153786&Mask=200#Refs>, retrieved on Jan. 30, 2024, 3 pages.
U.S. Appl. No. 17/835,676, Wang, Fluorescent Dye Oil Tracer Compositions, filed Jun. 8, 2022, 59 pages.

* cited by examiner

Molecular Barcode

Fluorophore

Fluorophore

Molecular Barcode

FLUORESCENT DYE MOLECULES FOR TRACER APPLICATIONS IN SUBTERRANEAN FORMATIONS

TECHNICAL FIELD

This disclosure relates to methods and compositions used in generating and using functionalized fluorescent tracers in drilling and oil well applications.

BACKGROUND

Tracer techniques can be a powerful diagnostic tool in numerous scientific disciplines and for technologies in many industrial sectors. Molecular tracers can include water-soluble or oil-soluble compounds. In field tests of oilfields, water-soluble tracers can provide a better understanding of the studied oil reservoir, for example, a better understanding of inter-well connections, connections between layers and heterogeneities. Similarly, oil-soluble tracers can provide information on petroleum products, for example qualitative analysis of the production fluid return from multiple stage completions, either vertical or horizontal completions.

SUMMARY

This disclosure describes technologies relating to functionalized fluorescent tracers, methods of making the tracers, and methods of using the tracers. Certain aspects of the subject matter described can be implemented as a composition. The composition includes a functionalized fluorescent dye. The functionalized fluorescent dye includes an isothiocyanate-containing dye functionalized with a functional group. The functional group includes an aromatic compound with a primary amine. The isothiocyanate-containing dye is selected from the group consisting of fluorescein isothiocyanate, Rhodamine B isothiocyanate, or tetramethylrhodamine isothiocyanate, or any isoform thereof. The functional group is selected from 1-naphthylamine, 2-aminoanthracene, 1-aminopyrene, 6-chrysenamine, 9-aminophenanthrene, 2-aminofluorene, 9-aminoacridine, 1,10-phenanthrolin-5-amine, 9H-carbazol-2-amine, or 3-amino-9-ethylcarbazole.

This, and other aspects, can include one or more of the following features. In some implementations, the isothiocyanate-containing dye is Rhodamine B isothiocyanate, and the functional group is 1,10-phenanthrolin-5-amine. In some implementations, isothiocyanate-containing dye is fluorescein isothiocyanate, and the functional group is 1-aminopyrene. In some implementations, isothiocyanate-containing dye is tetramethylrhodamine isothiocyanate, and the functional group is 2-aminofluorene.

Certain aspects of the subject matter described can be implemented as a method for making a functionalized fluorescent dye. A water-soluble isothiocyanate-containing fluorescent dye is dissolved in an aqueous solvent to yield an aqueous dye solution. The water-soluble isothiocyanate-containing fluorescent dye is selected from the group consisting of fluorescein isothiocyanate, Rhodamine B isothiocyanate, or tetramethylrhodamine isothiocyanate, or any isoform thereof. A functional group is dissolved in an organic solvent to yield an organic functional group solution. The functional group includes an aromatic compound with a primary amine. The functional group is selected from the group consisting of 1-naphthylamine, 2-aminoanthracene, 1-aminopyrene, 6-chrysenamine, 9-aminophenanthrene, 2-aminofluorene, 9-aminoacridine, 1,10-phenanthrolin-5-amine, 9H-carbazol-2-amine, or 3-amino-9-ethylcarbazole. The aqueous dye solution and the organic functional group solution are mixed to form an emulsion. The emulsion is separated into an aqueous phase and an organic phase. The functionalized fluorescent dye is extracted from the organic phase. The functionalized fluorescent dye is a reaction product of the water-soluble isothiocyanate-containing dye and the functional group.

This, and other aspects, can include one or more of the following features. The aqueous solvent can be deionized water. The aqueous solvent can be a mixture of water and ethanol. In some implementations, a volumetric ratio of water to ethanol of the aqueous solvent is about 9:1. The organic solvent can be chloroform, cyclohexane, or a combination thereof. Extracting the functionalized fluorescent dye from the organic phase can include evaporating the organic solvent.

Certain aspects of the subject matter described can be implemented as a method of tracing fluid flow in a subterranean formation. A functionalized fluorescent tracer and a fluid are mixed to form a tracer fluid. The functionalized fluorescent tracer includes an isothiocyanate-containing dye functionalized with a functional group. The functional group includes an aromatic compound with a primary amine. The isothiocyanate-containing dye is selected from the group consisting of fluorescein isothiocyanate, Rhodamine B isothiocyanate, or tetramethylrhodamine isothiocyanate, or any isoform thereof. The functional group is selected from the group consisting of 1-naphthylamine, 2-aminoanthracene, 1-aminopyrene, 6-chrysenamine, 9-aminophenanthrene, 2-aminofluorene, 9-aminoacridine, 1,10-phenanthrolin-5-amine, 9H-carbazol-2-amine, or 3-amino-9-ethylcarbazole. The tracer fluid is flowed into a first subterranean formation. A sample is recovered from the first subterranean formation or a second subterranean formation that is connected to the first subterranean formation. The sample is analyzed for a fluorescent signal.

This, and other aspects, can include one or more of the following features. The functionalized fluorescent tracer can be identified in the sample using fluorescence (for example, fluorescence spectroscopy or fluorescence imaging), ultraviolet-visible (UV-Vis) spectroscopy, Fourier-transform infrared spectroscopy (FTIR), Raman spectroscopy, mass spectroscopy (MS), high performance liquid chromatography (HPLC), liquid chromatography-mass spectroscopy (LC-MS), or pyrolysis gas chromatography-mass spectrometry (pyrolysis GC-MS), or any combination thereof. The sample can be a fluid sample, a solid sample, or a sample that includes both fluid and solid. The fluid (mixed with the functionalized fluorescent tracer) can be a fracking fluid or a drilling mud.

The details of one or more implementations of the subject matter of this disclosure are set forth in the accompanying drawings and the description. Other features, aspects, and advantages of the subject matter will become apparent from the description, the drawings, and the claims.

DETAILED DESCRIPTION

This disclosure describes functionalized fluorescent tracers, methods of making the tracers, and methods of using the tracers. The functionalized fluorescent tracers can be used, for example, to track hydrocarbons in wells. A chemical method can be implemented to modify the structures of conventional fluorescent dye molecules by covalently bonding an aromatic compound to the dye molecule, which can increase the fluorescent dye's hydrophobicity. The resulting dye is oil-soluble while retaining its fluorescence. The aromatic compound can also serve as a molecular identifier.

Figure 1:
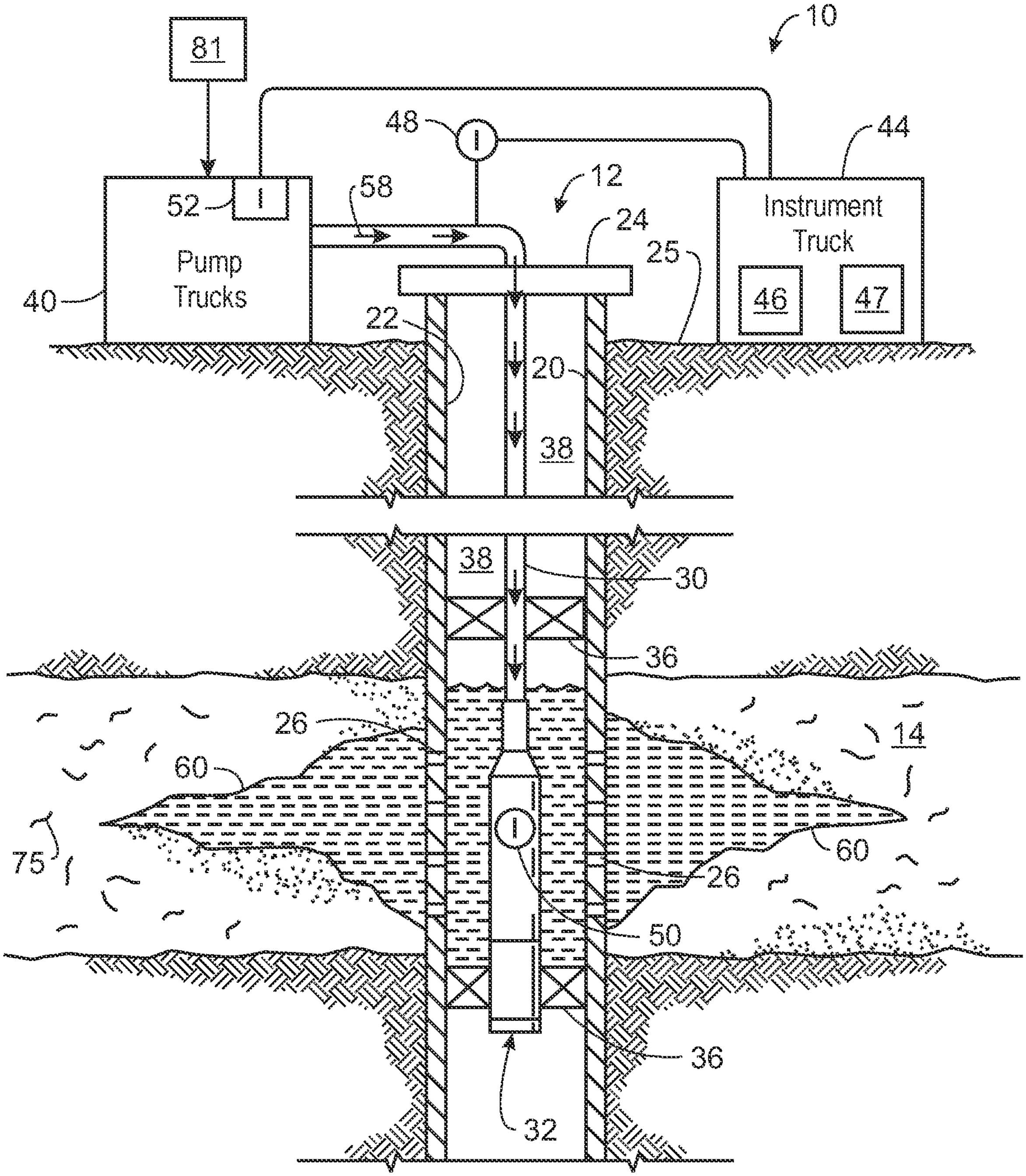
FIG. 1 is a schematic diagram of an example well.

FIG. 1 depicts an example of a drilling operation 10 for a well 12. The well 12 can be in a wellbore 20 formed in a subterranean zone 14 of a geological formation in the Earth's crust. The well 12 enables access to the subterranean zone 14 to allow recovery (that is, production) of fluids to the surface and, in some implementations, additionally or alternatively allows fluids to be placed in the Earth. The subterranean zone 14 can include, for example, a formation, a portion of a formation, or multiple formations in a hydrocarbon-bearing reservoir from which recovery operations can be practiced to recover trapped hydrocarbons. Examples of unconventional reservoirs include tight-gas sands, gas and oil shales, coalbed methane, heavy oil and tar sands, gas-hydrate deposits, to name a few. In some implementations, the subterranean zone 14 includes an underground formation including natural fractures 60 in rock formations containing hydrocarbons (for example, oil, gas, or both). For example, the subterranean zone 14 can include a fractured shale. In some implementations, the well 12 can intersect other suitable types of formations, including reservoirs that are not naturally fractured.

The well 12 can include a casing 22 and well head 24. The wellbore 20 can be a vertical, horizontal, deviated, or multilateral bore. The casing 22 can be cemented or otherwise suitably secured in the wellbore 20. Perforations 26 can be formed in the casing 22 at the level of the subterranean zone 14 to allow oil, gas, and by-products to flow into the well 12 and be produced to the surface 25. Perforations 26 can be formed using shape charges, a perforating gun, or otherwise.

For a drilling treatment 10, a work string 30 can be disposed in the wellbore 20. The work string 30 can be coiled tubing, sectioned pipe, or other suitable tubing. A drilling tool or drill bit 32 can be coupled to an end of the work string 30. Packers 36 can seal an annulus 38 of the wellbore 20 uphole of and downhole of the subterranean zone 14. Packers 36 can be mechanical, fluid inflatable, or other suitable packers.

One or more pump trucks 40 can be coupled to the work string 30 at the surface 25. The pump trucks 40 pump drilling mud 58 down the work string 30 to lubricate and cool the drilling tool or drill bit 32, maintain hydrostatic pressure in the wellbore, and carry subterranean cuttings to the surface. The drilling mud 58 can include a fluid pad, proppants, flush fluid, or a combination of these components. The pump trucks 40 can include mobile vehicles, equipment such as skids, or other suitable structures.

One or more instrument trucks 44 can also be provided at the surface 25. The instrument truck 44 can include a drilling control system 46 and a drilling simulator 47. The drilling control system 46 monitors and controls the drilling treatment 10. The drilling control system 46 can control the pump trucks 40 and fluid valves to stop and start the drilling treatment 10. The drilling control system 46 communicates with surface and subsurface instruments to monitor and control the drilling treatment 10. In some implementations, the surface and subsurface instruments may comprise surface sensors 48, down-hole sensors 50, and pump controls 52.

Additives 81 can be mixed with drilling mud 58 or other drilling fluids and flowed through the reservoir. In some implementations, the additives 81 can include one or more tracers, for example, a fluorescent dye. Fluorescent dyes can be used as water-soluble tracers. These dyes are inexpensive and easy to use. Examples of fluorescent dyes include fluorescein, eosin, Rhodamine, and Rhodamine-B. However, these organic dye-based tracers have some shortcomings as oil-soluble tracers. For example, the water-soluble tracers fluorescein, eosin, and Rhodamine can adsorb onto reservoir rock or partition with the oil phase. In oil, these tracers have poor solubility due to their high hydrophilicity, although the molecules may partially dissolve in the oil phase. In addition, the number of tracers is limited to the number of organic dye molecules available.

The tracers described herein overcome these shortcomings. These tracers can be generated using a synthetic method to tune the hydrophilicity/hydrophobicity of water-soluble dye molecules by chemically modifying the molecular structure of the molecule. For example, by covalently grafting functional groups onto the dye molecules, the various functional groups can create barcoded structural information, resulting in new compounds. In some embodiments, by introducing hydrophobic functional groups (for example, an aromatic functional group) into water-soluble dye molecules, the hydrophobicity of the resulting molecules can be enhanced, thus improving their solubility in an oil phase. By tailoring the molecules, the hydrophilicity and hydrophobicity of the molecule can be adjusted to a desired degree. Therefore, the partition of the molecule in an oil phase is controllable. This, in part, enables the potential application of these functionalized fluorescent dyes as partition tracers for oil reservoir applications. The structure-modified dyes reserve their fluorescence properties, although in some implementations the fluorescence features may also be modified by the introduction of functional groups.

These functionalized fluorescent dyes are described herein as barcoded or having barcode information. In this context, "barcode" refers to the fact that these functionalized dyes or tracers are uniquely identifiable two or more orthogonal analyses. As a first factor, the tracers can be identified by their fluorescence signal, for example, by the wavelength of the emission spectrum or simply by the presence of a fluorescent signal. As a second factor, the tracers can be identified by their mass or hydrophobicity. Accordingly, the unique combinations of the different fluorophores and the different functionalization groups results in a library of barcoded tracers.

Barcoded tracers have several advantages. For example, different combinations of different tracers can be used simultaneously or in parallel to provide information about drilling operations or subterranean formations. For example, two or more uniquely identifiable tracers can be injected at two or more different drilling sites and can yield information about inter well connectivity. In another example, uniquely identifiable tracers can be injected at the same drilling site at different times, can yield temporal information about transit time, depth, or length of subterranean fractures or formations.

Further, the two-factor nature of the barcode tracers allows for an advantageous two-factor analysis. The first factor, the fluorescence signal, can be detected in an initial, rapid analysis (for example, by fluorescence spectroscopy or fluorescence imaging). Accordingly, samples recovered from a drilling operation or subterranean formation can be quickly and qualitative analyzed for the presence of a fluorescence signal, i.e., a 'yes/no' analysis. In some implementations, this first analysis can be done on-site, and samples exhibiting a fluorescence signal can be allocated for further processing. Next, the samples exhibiting a fluorescence signal can be subsequently separated and analyzed by mass or chromatographic methods, for example by high performance liquid chromatography (HPLC), mass spectrometry (MS), liquid chromatography-mass spectrometry (LC-MS) analysis, or pyrolysis gas chromatography-mass spectrometry (pyrolysis GC-MS).

A chemical method to modify the structures of conventional dye molecules by introducing molecular barcode information and by tailoring the hydrophilicity and/or hydrophobicity of the conventional water-soluble dye molecules is described herein. The resulting compounds expand the number of dyes available for tracer applications as water-soluble tracers, oil tracers, or partition tracers.

The new dye molecules include the general structure $R_1$—X—Ru, where $R_1$ is a fluorescent fluorophore. The fluorophore can be either hydrophilic or hydrophobic, and can be detectable by optical methods, for example, fluorescence imaging or molecular spectroscopy (absorbance or fluorescence). In the general structure, X can be a linking molecule. X can be selected from the group that includes $C_{1-18}$ alkylene, $C_{1-18}$ alkenylene, or $C_{1-18}$ alkynylene, where each of $C_{1-18}$ alkylene, $C_{1-18}$ alkenylene, or $C_{1-18}$ alkynylene can be optionally replaced or interrupted by any one of oxygen (O), sulfur (S), or an amine (NH). In some implementations, X is a thiourea. In the general structure, $R_{II}$ can be selected from the group that includes hydrogen, alkoxy, haloalkoxy (including Cl, Br, or I), aryl, or heteroaryl (including N, NH, O, or S). The Ru confers a molecular fingerprint or barcode structure into the new compounds. The $R_1$—X—Ru compounds are detectable by spectroscopy and imaging methods, for example, UV-Visible spectroscopy (UV-Vis), fluorescence (such as fluorescence spectroscopy or fluorescence imaging), Fourier-transform infrared spectroscopy (FTIR), Raman spectroscopy, mass spectroscopy, or chromatography (such as HPLC, LC-MS, or pyrolysis GC-MS).

In some implementations, the fluorescent dye $R_1$ is fluorescein isothiocyanate (FITC), Rhodamine B isothiocyanate (RBITC), tetramethylrhodamine isothiocyanate (MRITC or TRITC), 1,1'-bis(3-isothiocyanatopropyl)-11-chloro-4,5:4',5'-dibenzo-3,3,3',3'-tetramethyl-10,12-trimethylenindotricarbocyanine bromide (NIR 5e), eosin-5-isothiocyanate, or any isomer thereof. The structures of FITC, RBITC, and MRITC/TRITC are shown in Table 1. These dyes are highly water-soluble, i.e., hydrophilic, and have fluorescence emissions in the visible light spectral region. The excitation and emission wavelengths (in nanometers, nm) of these dyes are listed in Table 1.

TABLE 1

| Water-Soluble Dyes and their Molecular Structure | | | |
|---|---|---|---|
| Dye compound | Molecular structure; Molecular weight | Fluorescence $\lambda_{excitation}/\lambda_{emission}$ | CAS Number/ Isomers |
| Fluorescein isothiocyanate (FITC) | 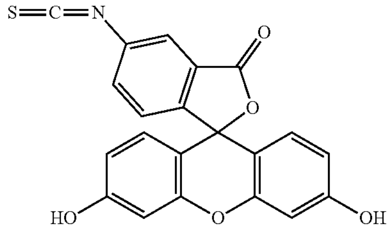 MW = 389.38 | 495 nm/519 nm | 27072-45-3 (mixed isomers); 3326-32-7 (5-isomer); 18861-78-4 (6-isomer) |
| Rhodamine B isothiocyanate (RBITC) | 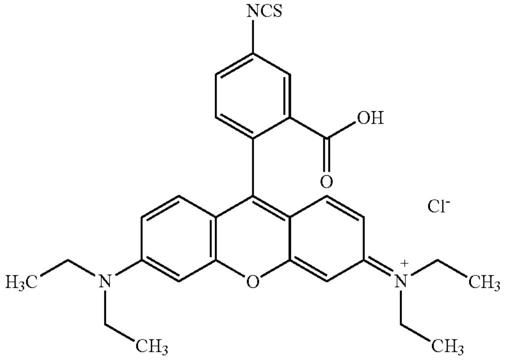 MW = 536.08 | 570 nm/595 nm | 36877-69-7 (mixed isomers) |

TABLE 1-continued

| Water-Soluble Dyes and their Molecular Structure | | | |
|---|---|---|---|
| Dye compound | Molecular structure; Molecular weight | Fluorescence $\lambda_{excitation}/\lambda_{emission}$ | CAS Number/ Isomers |
| Tetramethylrhodamine isothiocyanate (MRITC or TRITC) | 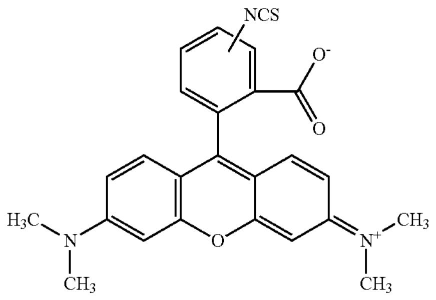 MW = 443.52 | 544 nm/570 nm | 95197-95-8 (mixed isomers); 80724-20-5 (Isomer R); 80724-19-2 (5-TRITC) |

The dyes shown in Table 1 were each modified with additional functional groups. The functional groups are added using the reaction of a primary amine with an isothiocyanate to result in a substituted thiourea, as shown in Equation 1.

(Eq. 1)

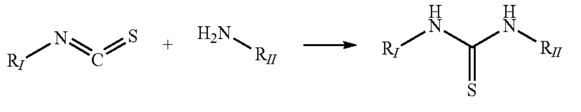

$R_{II}$ is an alkyl, aromatic, heterocyclic group, or other suitable amine-containing functional group, and $R_I$ is the isothiocyanate-containing fluorescent dye, where in Equation 1 the isothiocyanate group is expanded for clarity.

Figure 2:
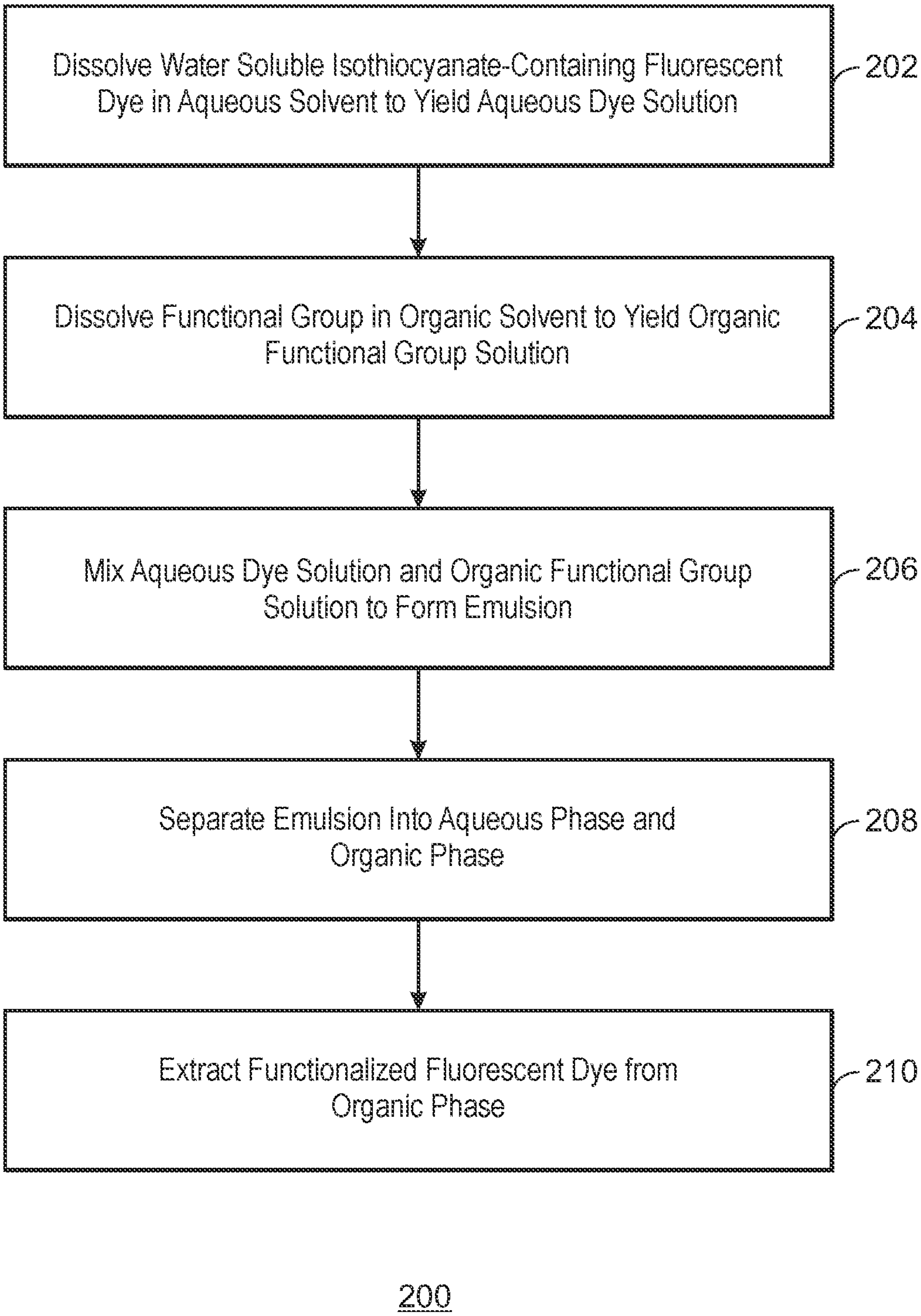
FIG. 2 is a flow chart of an example method for making a functionalized fluorescent dye that can be used in the well of FIG. 1.

FIG. 2 is a flow chart of an example method 200 of making a functionalized fluorescent dye. The reactions were performed at room temperature in a bi-phase system. At block 202, a water-soluble isothiocyanate-containing fluorescent dye (such as FITC, RBITC, MRITC, or TRITC) is dissolved in an aqueous solvent to yield an aqueous dye solution. In some implementations, the aqueous dye solution at block 202 is deionized water. In some implementations, the aqueous dye solution at block 202 is a mixture of water and ethanol. For example, the aqueous dye solution at block 202 can be a water/ethanol mixture with a 9:1 volumetric ratio of water to ethanol. At block 204, a functional group is dissolved in an organic solvent to yield an organic functional group solution. The functional group at block 204 is an oil-soluble functional group that includes an amino group. For example, the functional group at block 204 includes an aromatic (heterocyclic) compound with a primary amine. The organic solvent at block 204 is any organic solvent in which the functional group is soluble. For example, an aromatic amine compound (from Table 2) can be dissolved in chloroform or cyclohexane at block 204. The aqueous dye solution and the organic functional group solution each contain the same molecular molar concentration of fluorescent dye and aromatic amine compound, respectively. At block 206, the aqueous dye solution and the organic functional group solution are mixed to form an emulsion. In some implementations, the aqueous dye solution and the organic functional group solution are mixed in equal volumes at block 206 and stirred vigorously until the solutions form an emulsion. In some implementations, the reaction between the fluorescent dye and the functional group is allowed to continue under stirring for at least 12 hours at block 206. At block 208, the emulsion is separated into an aqueous phase and an organic phase. For example, the stirring is stopped, and the emulsion is allowed to settle into two phases at block 208. At block 210, the functionalized fluorescent dye is extracted from the organic phase. The functionalized fluorescent dye extracted at block 210 is a reaction product of the water-soluble isothiocyanate-containing dye and the functional group. It can be observed, for example, by color that the dye is transferred from the aqueous phase to the organic phase due to the reaction, which covalently bonds the hydrophobic functional group to the fluorescent dye. In some implementations, extracting the functionalized fluorescent dye from the organic phase at block 210 includes evaporating the organic solvent by nitrogen bubbling, heating, or both. The obtained solid powder (functionalized fluorescent dye) can be re-dispersed into a different organic solvent, such as crude oil, methanol, ethanol, propanol, isopropanol, butanol, pentanol, hexanol, heptanol, octanol, acetone, ethyl acetate, acetonitrile, chloroform, dichloromethane, hexane, heptane, octane, cyclohexane, benzene, toluene, tetrahydrofuran, or any combination of these.

Table 2 illustrates different aromatic amine-containing functional groups that can be used to functionalize an isothiocyanate dye. The compounds shown in Table 2 are aromatic compounds with primary amino groups. The compounds have different molecular weights and provide both barcode information and the ability to tailor the hydrophobicity and miscibility with oils of the resulting compound, based on, for example, the number of cyclic rings. Accordingly, isothiocyanate dyes functionalized with the compounds listed in Table 2 can have variable partitioning in oil phases.

TABLE 2

| Aromatic Compounds with Primary Amino Groups | | |
|---|---|---|
| Compound | Molecular Structure/Weight (Daltons) | CAS number |
| 1-naphthylamine | 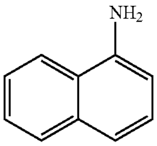 143.18 | 134-32-7 |
| 2-aminoanthracene | 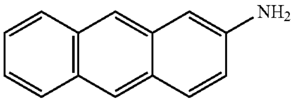 193.24 | 613-13-8 |
| 1-aminopyrene | 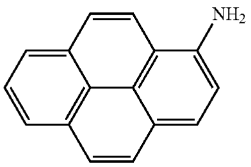 217.26 | 1606-67-3 |
| 6-chrysenamine | 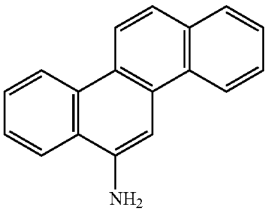 243.3 | 2642-98-0 |
| 9-aminophenanthrene | 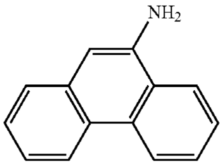 193.24 | 947-73-9 |
| 2-aminofluorene | 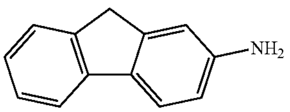 181.23 | 153-78-6 |
| 9-aminoacridine | 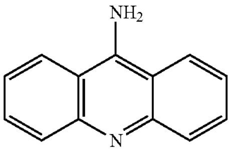 194.23 | 90-45-9 |

TABLE 2-continued

| Aromatic Compounds with Primary Amino Groups | | |
|---|---|---|
| Compound | Molecular Structure/Weight (Daltons) | CAS number |
| 1,10-phenanthrolin-5-amine | 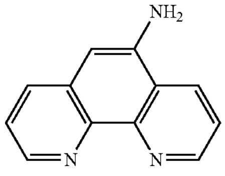 195.22 | 54258-41-2 |
| 9H-carbazol-2-amine (hydrochloride) | 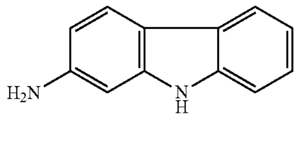 218.68 | 63716-35-8 |
| 3-amino-9-ethylcarbazole | 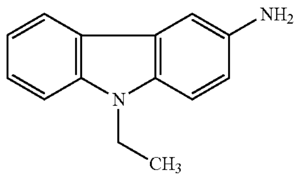 210.27 | 132-32-1 |

The dyes described herein can be used as tracers in subterranean applications. For example, multistage hydraulic fracturing along a horizontal well is key to effectively recover hydrocarbons from tight reservoirs. Improving the hydrocarbon recovery requires detailed production information of each hydraulic fracture. Water-soluble chemical tracers are often used to calculate the production profile from multistage fracturing through a tracer flow back test, whereas oil-soluble tracers are used as a direct indicator to estimate the oil production contribution in individual fractures stages, for example, diagnosis of multi-zone oil flow efficiency, confirming zonal oil flow, or qualifying flow assurance. Oil-soluble tracers can also be embedded in the porous media and absorbed on the surfaces of solid carriers, which allows the tracers to be released from their carriers when oil passes through and has negligible partitioning into the water or gas phase.

With the barcoded oil-soluble tracers described herein, qualitative analysis by fluorescence spectroscopy or imaging can be used for early screening if the tracer is in the oil flow from each stage, while detailed molecular barcode information can be revealed by HPLC or LC-MS analysis to identify each tracers from different locations. Further, these synthesized barcoded oil-soluble compounds can also be added to mud formulations in drilling fluids as mud tracers for mud logging applications.

Figure 3:
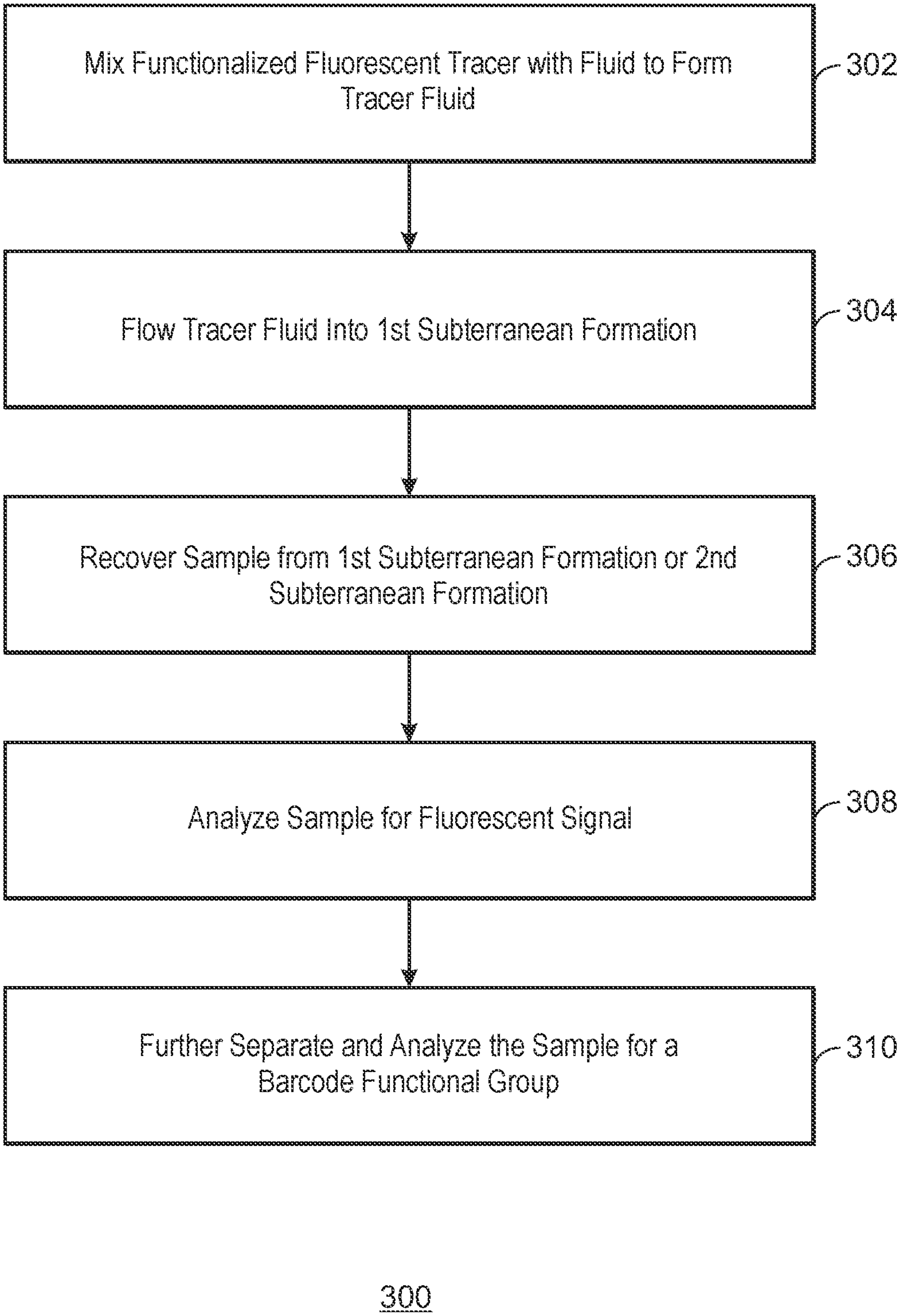
FIG. 3 is a flow chart of an example method for treating a well.

FIG. 3 is a flow chart of an example method 300 of tracing fluid flow in a subterranean formation. At block 302, a functionalized fluorescent tracer and a fluid are mixed to form a tracer fluid. At block 304, the tracer fluid is flowed into a first subterranean formation. At block 306, a sample is recovered from the first subterranean formation or a second subterranean formation connected to the first subterranean formation. At block 308, the sample is analyzed for a fluorescent signal. At block 310, the sample is further separated and analyzed for a barcode functional group. For example, the sample is analyzed at block 310 to identify the barcode functional group present in the functionalized fluorescent tracer.

Example 1

Figure 4:
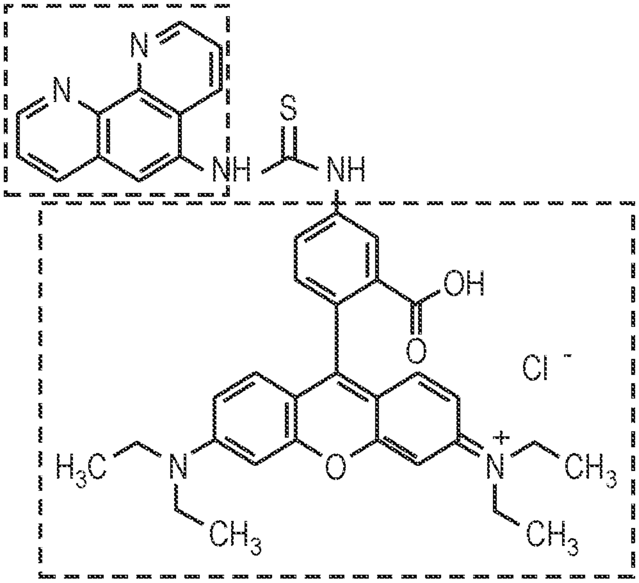
FIG. 4 is a molecular structure of an example functionalized fluorescent dye.

1.5 milligrams (mg) of 1,10-phenanthrolin-5-amine was dissolved in 50 milliliters (mL) of chloroform. 53.6 mg of RBITC was dissolved in 50 mL of deionized water. The two solutions were mixed in a round bottom flask and reacted for more than 12 hours under vigorous stirring by a magnetic stirrer. Upon completion of the reaction, the reaction mixture was transferred into a separating funnel and left to sit overnight for phase separation. The chloroform phase was separated and collected. The chloroform was evaporated by nitrogen bubbling, and the solid powder sample was collected for further re-dissolving in a different organic solvent. The molecular structure of the functionalized fluorescent dye is shown in FIG. 4.

Example 2

Figure 5:
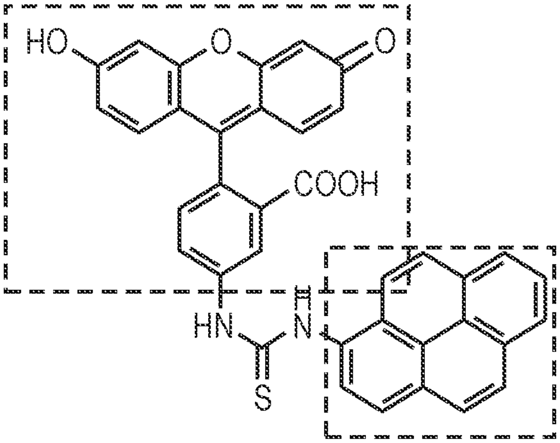
FIG. 5 is a molecular structure of an example functionalized fluorescent dye.

21.7 mg of 1-aminopyrene was dissolved in 50 mL of chloroform. 38.9 mg of FITC was dissolved in 50 mL of a water/ethanol mixture with a 9:1 volumetric ratio of water to ethanol. The two solutions were mixed in a round bottom flask and reacted for more than 12 hours under vigorous stirring by a magnetic stirrer. Upon completion of the reaction, the reaction mixture was transferred into a separating funnel and left to sit overnight for phase separation. The chloroform phase was separated and collected. The chloroform was evaporated by nitrogen bubbling, and the solid powder sample was collected for further re-dissolving in a different organic solvent. The molecular structure of the functionalized fluorescent dye is shown in FIG. 5.

Example 3

Figure 6:
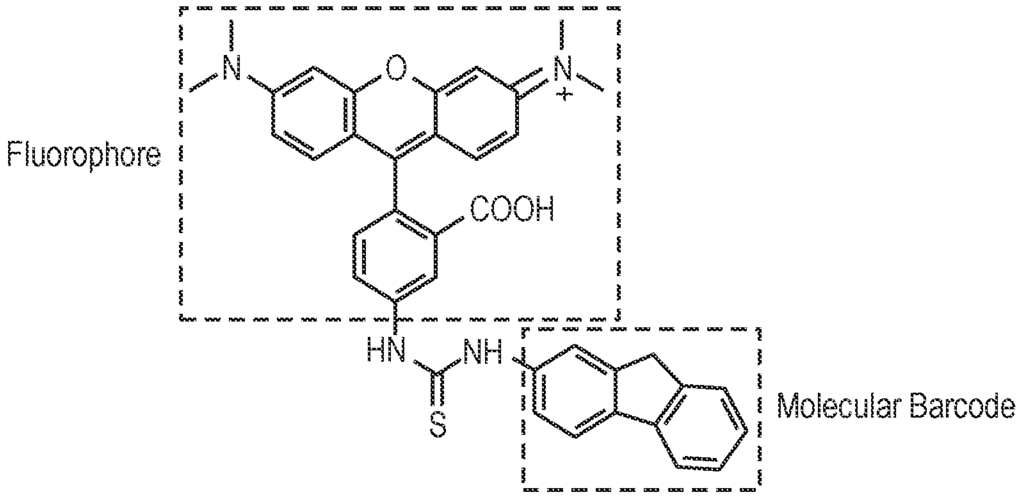
FIG. 6 is a molecular structure of an example functionalized fluorescent dye.

18.1 mg of 2-aminofluorene was dissolved in 50 mL of cyclohexane. 44.4 mg of TRITC was dissolved in 50 mL of water. The two solutions were mixed in a round bottom flask and reacted for 6 hours under vigorous stirring by a magnetic stirrer. Upon completion of the reaction, the reaction mixture was transferred into a separating funnel and left to sit overnight for phase separation. The cyclohexane phase was separated and collected. The cyclohexane was evaporated by nitrogen bubbling, and the solid powder sample was collected for further re-dissolving in a different organic solvent. The molecular structure of the functionalized fluorescent dye is shown in FIG. 6.

Examples 1, 2, and 3 provide example procedures for making a functionalized fluorescent dye. With similar procedures, any one of the organic, fluorescent dyes shown in Table 1 can be combined with any one of the aromatic functional groups containing primary amino groups shown in Table 2. The following includes example combinations of organic, fluorescent dyes and aromatic functional groups that can be combined to make a functionalized fluorescent dye. FITC and 1-naphthylamine can be combined to make a functionalized fluorescent dye. FITC and 2-aminoanthracene can be combined to make a functionalized fluorescent dye. FITC and 6-chrysenamine can be combined to make a functionalized fluorescent dye. FITC and 9-aminophenanthrene can be combined to make a functionalized fluorescent dye. FITC and 2-aminofluorene can be combined to make a functionalized fluorescent dye. FITC and 9-aminoacridine can be combined to make a functionalized fluorescent dye. FITC and 1,10-phenanthrolin-5-amine can be combined to make a functionalized fluorescent dye. FITC and 9H-carbazol-2-amine can be combined to make a functionalized fluorescent dye. FITC and 3-amino-9-ethylcarbazole can be combined to make a functionalized fluorescent dye. RBITC and 1-naphthylamine can be combined to make a functionalized fluorescent dye. RBITC and 2-aminoanthracene can be combined to make a functionalized fluorescent dye. RBITC and 1-aminopyrene can be combined to make a functionalized fluorescent dye. RBITC and 6-chrysenamine can be combined to make a functionalized fluorescent dye. RBITC and 9-aminophenanthrene can be combined to make a functionalized fluorescent dye. RBITC and 2-aminofluorene can be combined to make a functionalized fluorescent dye. RBITC and 9-aminoacridine can be combined to make a functionalized fluorescent dye. RBITC and 9H-carbazol-2-amine can be combined to make a functionalized fluorescent dye. RBITC and 3-amino-9-ethylcarbazole can be combined to make a functionalized fluorescent dye. TRITC and 1-naphthylamine can be combined to make a functionalized fluorescent dye. TRITC and 2-aminoanthracene can be combined to make a functionalized fluorescent dye. TRITC and 1-aminopyrene can be combined to make a functionalized fluorescent dye. TRITC and 6-chrysenamine can be combined to make a functionalized fluorescent dye. TRITC and 9-aminophenanthrene can be combined to make a functionalized fluorescent dye. TRITC and 9-aminoacridine can be combined to make a functionalized fluorescent dye. TRITC and 1,10-phenanthrolin-5-amine can be combined to make a functionalized fluorescent dye. TRITC and 9H-carbazol-2-amine can be combined to make a functionalized fluorescent dye. TRITC and 3-amino-9-ethylcarbazole can be combined to make a functionalized fluorescent dye.

While this specification contains many specific implementation details, these should not be construed as limitations on the scope of what may be claimed, but rather as descriptions of features that may be specific to particular implementations. Certain features that are described in this specification in the context of separate implementations can also be implemented, in combination, in a single implementation. Conversely, various features that are described in the context of a single implementation can also be implemented in multiple implementations, separately, or in any subcombination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

As used in this disclosure, the terms "a," "an," or "the" are used to include one or more than one unless the context clearly dictates otherwise. The term "or" is used to refer to a nonexclusive "or" unless otherwise indicated. The statement "at least one of A and B" has the same meaning as "A, B, or A and B." In addition, it is to be understood that the phraseology or terminology employed in this disclosure, and not otherwise defined, is for the purpose of description only and not of limitation. Any use of section headings is intended to aid reading of the document and is not to be interpreted as limiting; information that is relevant to a section heading may occur within or outside of that particular section.

As used in this disclosure, the term "about" or "approximately" can allow for a degree of variability in a value or range, for example, within 10%, within 5%, or within 1% of a stated value or of a stated limit of a range.

As used in this disclosure, the term "substantially" refers to a majority of, or mostly, as in at least about 50%, 60%, 70%, 80%, 90%, 95%, 96%, 97%, 98%, 99%, 99.5%, 99.9%, 99.99%, or at least about 99.999% or more.

Values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "0.1% to about 5%" or "0.1% to 5%" should be interpreted to include about 0.1% to about 5%, as well as the individual values (for example, 1%, 2%, 3%, and 4%) and the sub-ranges (for example, 0.1% to 0.5%, 1.1% to 2.2%, 3.3% to 4.4%) within the indicated range. The statement "X to Y" has the same meaning as "about X to about Y," unless indicated otherwise. Likewise, the statement "X, Y, or Z" has the same meaning as "about X, about Y, or about Z," unless indicated otherwise.

The term "downhole" as used in this disclosure refers to under the surface of the earth, such as a location within or fluidly connected to a wellbore.

As used in this disclosure, the term "drilling fluid" refers to fluids, slurries, or muds used in drilling operations downhole, such as during the formation of the wellbore.

As used in this disclosure, the term "fluid" refers to gases, liquids, gels, and any combination of these, unless otherwise indicated.

As used in this disclosure, the term "subterranean material" or "subterranean zone" or "subterranean formation" refers to any material under the surface of the earth, including under the surface of the bottom of the ocean. For example, a subterranean zone or material can be any section of a wellbore and any section of a subterranean petroleum- or water-producing formation or region in fluid contact with the wellbore. Placing a material in a subterranean zone can include contacting the material with any section of a wellbore or with any subterranean region in fluid contact the material. Subterranean materials can include any materials placed into the wellbore such as cement, drill shafts, liners, tubing, casing, or screens; placing a material in a subterranean zone can include contacting with such subterranean materials. In some examples, a subterranean zone or material can be any downhole region that can produce liquid and/or gaseous petroleum materials, water, or any downhole section in fluid contact with liquid or gaseous petroleum materials, or water. For example, a subterranean zone or material can be at least one of an area desired to be fractured, a fracture or an area surrounding a fracture, and a flow pathway or an area surrounding a flow pathway, in which a fracture or a flow pathway can be optionally fluidly connected to a subterranean petroleum- or water-producing region, directly or through one or more fractures or flow pathways.

As used in this disclosure, "treatment of a subterranean zone" can include any activity directed to extraction of water or petroleum materials from a subterranean petroleum- or water-producing formation or region, for example, including drilling, stimulation, hydraulic fracturing, clean-up, acidizing, completion, cementing, remedial treatment, abandonment, aquifer remediation, identifying oil rich regions via imaging techniques, and the like.

As used in this disclosure, a "flow pathway" downhole can include any suitable subterranean flow pathway through which two subterranean locations are in fluid connection. The flow pathway can be sufficient for petroleum and/or water to flow from one subterranean location to the wellbore or vice-versa. A flow pathway can include at least one of a hydraulic fracture, and a fluid connection across a screen, across gravel pack, across proppant, including across resin-bonded proppant or proppant deposited in a fracture, and across sand. A flow pathway can include a natural subterranean passageway through which fluids can flow. In some implementations, a flow pathway can be a water source and can include water. In some implementations, a flow pathway can be a petroleum source and can include petroleum. In some implementations, a flow pathway can be sufficient to divert water, a downhole fluid, or a produced hydrocarbon from a wellbore, fracture, or flow pathway connected to the pathway.

As used in this disclosure, "weight percent" (wt. %) can be considered a mass fraction or a mass ratio of a substance to the total mixture or composition. Weight percent can be a weight-to-weight ratio or mass-to-mass ratio, unless indicated otherwise.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking or parallel processing (or a combination of multitasking and parallel processing) may be advantageous and performed as deemed appropriate.

Moreover, the separation or integration of various system modules and components in the previously described implementations should not be understood as requiring such separation or integration in all implementations, and it should be understood that the described components and systems can generally be integrated together or packaged into multiple products.

Accordingly, the previously described example implementations do not define or constrain the present disclosure. Other changes, substitutions, and alterations are also possible without departing from the spirit and scope of the present disclosure.

What is claimed is:

1. A composition comprising:

a functionalized fluorescent dye, wherein the functionalized fluorescent dye is formed from an isothiocyanate-containing dye reacted with a primary amine, wherein:

the isothiocyanate-containing dye is selected from the group consisting of fluorescein isothiocyanate, an isomer thereof, Rhodamine B isothiocyanate, an isomer thereof, tetramethylrhodamine isothiocyanate, and an isomer thereof, and the primary amine is selected from the group consisting of 2-aminoanthracene, 6-chrysenamine, 9-aminophenanthrene, 2-aminofluorene, 9-aminoacridine, 9H-carbazol-2-amine, and 3-amino-9-ethylcarbazole.

2. The composition of claim 1, wherein the isothiocyanate-containing dye is tetramethylrhodamine isothiocyanate or an isomer thereof, and the primary amine is 2-aminofluorene.

3. The composition of claim 1, wherein the primary amine is 2-aminoanthracene, 1-aminopyrene, 6-chrysenamine, 9-aminophenanthrene, 2-aminofluorene, 9-aminoacridine, 9H-carbazol-2-amine, or 3-amino-9-ethylcarbazole.

4. The composition of claim 1, wherein the primary amine is 6-chrysenamine, 9-aminophenanthrene, or 2-aminoanthracene.

5. The composition of claim 1, wherein the primary amine is 2-aminofluorene, 9-aminoacridine, 9H-carbazol-2-amine, or 3-amino-9-ethylcarbazole.

6. A method of making a functionalized fluorescent dye, comprising:

dissolving a water-soluble isothiocyanate-containing fluorescent dye in an aqueous solvent to yield an aqueous dye solution, wherein the water-soluble isothiocyanate-containing fluorescent dye is selected from the group consisting of fluorescein isothiocyanate, or an isomer thereof, Rhodamine B isothiocyanate, or an isomer thereof, tetramethylrhodamine isothiocyanate, and an isomer thereof;

dissolving a primary amine in an organic solvent to yield a primary amine solution, wherein the primary amine is selected from the group consisting of 2-aminoanthracene, 6-chrysenamine, 9-aminophenanthrene, 2-aminofluorene, 9-aminoacridine, 9H-carbazol-2-amine, and 3-amino-9-ethylcarbazole;

mixing the aqueous dye solution and the primary amine solution to form an emulsion;

separating the emulsion into an aqueous phase and an organic phase; and extracting the functionalized fluorescent dye from the organic phase, wherein the functionalized fluorescent dye is a reaction product of the water-soluble isothiocyanate-containing dye and the primary amine.

7. The method of claim 6, wherein the aqueous solvent is deionized water.

8. The method of claim 6, wherein the aqueous solvent is a mixture of water and ethanol.

9. The method of claim 8, wherein a volumetric ratio of water to ethanol of the aqueous solvent is about 9:1.

10. The method of claim 6, wherein the organic solvent is chloroform.

11. The method of claim 6, wherein the organic solvent is cyclohexane.

12. The method of claim 6, wherein extracting the functionalized fluorescent dye from the organic phase comprises evaporating the organic solvent.

13. A method of tracing fluid flow in a subterranean formation, comprising:

mixing a functionalized fluorescent tracer and a fluid to form a tracer fluid, wherein the functionalized fluorescent tracer is formed from an isothiocyanate-containing dye reacted with a primary amine, wherein:

the isothiocyanate-containing dye is selected from the group consisting of fluorescein isothiocyanate, an isomer thereof, Rhodamine B isothiocyanate, an isomer thereof, tetramethylrhodamine isothiocyanate, and an isomer thereof; and the primary amine is selected from the group consisting of 2-aminoanthracene, 6-chrysenamine, 9-aminophenanthrene, 2-aminofluorene, 9-aminoacridine, 9H-carbazol-2-amine, and 3-amino-9-ethylcarbazole;

flowing the tracer fluid into a first subterranean formation;

recovering a sample from the first subterranean formation or a second subterranean formation connected to the first subterranean formation; and analyzing the sample for a fluorescent signal.

14. The method of claim 13, comprising identifying the functionalized fluorescent tracer in the sample using fluorescence spectroscopy, fluorescence imaging, ultraviolet-visible (UV-Vis) spectroscopy, Fourier-transform infrared spectroscopy (FTIR), Raman spectroscopy, mass spectrometry (MS), high performance liquid chromatography (HPLC), liquid chromatography-mass spectrometry (LC-MS), or pyrolysis gas chromatograph-mass spectrometry (pyrolysis GC-MS), or any combination thereof.

15. The method of claim 13, where in the sample is a fluid sample.

16. The method of claim 13, wherein the sample is a solid sample.

17. The method of claim 13, wherein the fluid is a fracking fluid.

18. The method of claim 13, wherein the fluid is a drilling mud.

* * * * *